United States Patent
Weitz et al.

(10) Patent No.: US 12,023,128 B2
(45) Date of Patent: Jul. 2, 2024

(54) SYSTEM AND METHOD FOR EYE TRACKING

(71) Applicant: IMMERSIX LTD, Tel Aviv (IL)

(72) Inventors: Ori Weitz, Tel-Aviv (IL); Saar Wilf, Tel-Aviv (IL)

(73) Assignee: IMMERSIX LTD., Tel Aviv (IL)

( * ) Notice: Subject to any disclaimer, the term of this patent is extended or adjusted under 35 U.S.C. 154(b) by 517 days.

(21) Appl. No.: 17/420,166

(22) PCT Filed: Jan. 5, 2020

(86) PCT No.: PCT/IL2020/050014
§ 371 (c)(1),
(2) Date: Jul. 1, 2021

(87) PCT Pub. No.: WO2020/141537
PCT Pub. Date: Jul. 9, 2020

(65) Prior Publication Data
US 2022/0148218 A1 May 12, 2022

Related U.S. Application Data

(60) Provisional application No. 62/788,068, filed on Jan. 3, 2019.

(51) Int. Cl.
*A61B 3/14* (2006.01)
*A61B 3/00* (2006.01)
(Continued)

(52) U.S. Cl.
CPC .......... *A61B 5/0077* (2013.01); *A61B 3/0008* (2013.01); *A61B 3/0025* (2013.01);
(Continued)

(58) Field of Classification Search
CPC ..... A61B 3/0008; A61B 3/0025; A61B 3/113; A61B 3/12; A61B 3/14; A61B 5/0077;
(Continued)

(56) References Cited

U.S. PATENT DOCUMENTS

| 5,644,642 A | 7/1997 | Kirschbaum |
| 10,168,531 B1 | 1/2019 | Trail et al. |

(Continued)

FOREIGN PATENT DOCUMENTS

| EP | 2644085 A1 | 10/2013 | |
| WO | WO-2010009450 A1 * | 1/2010 | ........... A61B 3/0025 |

(Continued)

OTHER PUBLICATIONS

Lisa Gottesfeld Brown "A survey of image registration techniques" ACM Computing Surveys, Dec. 1, 1992, pp. 325-376, vol. 24 No. 4, ACM, New York, NY, USA.

(Continued)

*Primary Examiner* — Mahidere S Sahle
(74) *Attorney, Agent, or Firm* — AlphaPatent Associates Ltd.; Daniel J. Swirsky

(57) ABSTRACT

A system and method for eye tracking includes receiving an input image including at least a portion of a person's retina, finding a spatial transformation between the input image and a reference image, the reference image including at least a portion of the person's retina and calculating a change in orientation of an eye of the person corresponding to the spatial transformation. A processor may calculate, from the change in orientation an orientation of the person's eye associated with the input image, a direction of gaze associated with the input image, a gaze target associated with the input image and/or a ray of gaze associated with the input image.

19 Claims, 12 Drawing Sheets

(51) Int. Cl.
*A61B 3/113* (2006.01)
*A61B 3/12* (2006.01)
*A61B 5/00* (2006.01)
*G06F 3/01* (2006.01)
*G06T 3/4038* (2024.01)
*G06T 7/00* (2017.01)
*G06T 7/246* (2017.01)
*G06T 7/50* (2017.01)
*G06T 7/73* (2017.01)
*G06V 10/141* (2022.01)
*G06V 10/74* (2022.01)
*G06V 10/75* (2022.01)
*G06V 40/18* (2022.01)
*H04N 23/56* (2023.01)
*H04N 23/90* (2023.01)
*G06F 18/22* (2023.01)

(52) U.S. Cl.
CPC ............... *A61B 3/113* (2013.01); *A61B 3/12* (2013.01); *A61B 3/14* (2013.01); *A61B 5/0062* (2013.01); *G06F 3/013* (2013.01); *G06T 3/4038* (2013.01); *G06T 7/0012* (2013.01); *G06T 7/248* (2017.01); *G06T 7/50* (2017.01); *G06T 7/74* (2017.01); *G06V 10/141* (2022.01); *G06V 10/75* (2022.01); *G06V 10/761* (2022.01); *G06V 40/18* (2022.01); *G06V 40/197* (2022.01); *H04N 23/56* (2023.01); *H04N 23/90* (2023.01); *A61B 5/6821* (2013.01); *G06F 18/22* (2023.01); *G06T 2207/10048* (2013.01); *G06T 2207/20081* (2013.01); *G06T 2207/30041* (2013.01)

(58) Field of Classification Search
CPC ..... A61B 5/0062; A61B 5/6821; G06F 3/013; G06F 18/22; G06T 3/4038; G06T 7/0012; G06T 7/248; G06T 7/50; G06T 7/74; G06T 2207/10048; G06T 2207/20081; G06T 2207/30041; G06V 10/141; G06V 10/75; G06V 10/761; G06V 40/18; G06V 40/197; H04N 23/56; H04N 23/90
USPC .................................. 351/209, 210; 382/103
See application file for complete search history.

(56) References Cited

U.S. PATENT DOCUMENTS

| | | |
|---|---|---|
| 10,175,485 B2 | 1/2019 | Kang et al. |
| 10,209,517 B2 | 2/2019 | Popovich |
| 10,420,464 B2 | 9/2019 | Wilf |
| 2012/0147328 A1 | 6/2012 | Yahav |
| 2013/0265547 A1* | 10/2013 | Higuchi ............... G01B 9/0203 351/208 |
| 2016/0081547 A1 | 3/2016 | Gramatikov |
| 2016/0210503 A1 | 7/2016 | Yin et al. |
| 2016/0278983 A1 | 9/2016 | Claus |
| 2016/0320837 A1 | 11/2016 | Swedish et al. |
| 2017/0007446 A1 | 1/2017 | Rill |
| 2017/0123489 A1* | 5/2017 | Guenter ............... A63F 13/213 |
| 2017/0188822 A1 | 7/2017 | Yang |
| 2018/0136486 A1 | 5/2018 | Macnamara |
| 2019/0056600 A1 | 2/2019 | Danziger et al. |
| 2019/0086674 A1 | 3/2019 | Sinay et al. |
| 2021/0049410 A1* | 2/2021 | Dierkes .................. G06N 3/08 |

FOREIGN PATENT DOCUMENTS

| | | | |
|---|---|---|---|
| WO | 2017/074807 A1 | 5/2017 | |
| WO | WO-2020055272 A1 * | 3/2020 | ........... A61B 3/0025 |

OTHER PUBLICATIONS

Extended European Search Report issued for EP20735868.0 on Mar. 22, 2022.

* cited by examiner

SYSTEM AND METHOD FOR EYE TRACKING

FIELD

The present invention relates to eye tracking based on images of a person's eye and retina.

BACKGROUND

Eye tracking to determine direction of gaze (also referred to as gaze tracking) may be useful in different fields, including human-machine interaction control of devices such as industrial machines, in aviation, and emergency room situations where both hands are needed for tasks other than operation of a computer, in virtual, augmented or extended reality applications, in computer games, in entertainment applications and also in research, to better understand subjects' behavior and visual processes. In fact, gaze tracking methods can be used in all the ways that people use their eyes.

A person's eye is a two-piece unit, composed of an anterior segment and a posterior segment. The anterior segment is made up of the cornea, iris and lens. The posterior segment is composed of the vitreous body, retina, choroid and the outer white shell called the sclera.

The pupil of the eye is the aperture located in the center of the iris, that lets light into the eye. The diameter of the pupil is controlled by the iris. Light entering through the pupil falls on the retina, which is the innermost light-sensitive layer coating the shell tissue of the eye. A small pit, the fovea, is located on the retina and is specialized for maximum visual acuity, which is necessary in humans for activities where visual detail is of chief importance, such as reading and identifying objects.

When an image of the world is formed on the retina, an image of the gaze target is formed on the fovea. That is, the location of the fovea corresponds to the gaze direction.

Video-based eye trackers exist. Typically, video-based tracking uses the corneal reflection and the center of the pupil as features from which to reconstruct the optical axis of the eye and/or as features to track in order to measure movement of the eye.

These methods are limited by image quality and/or variations of pupil size, for example, in response to ambient light. Furthermore, in these methods measurements are sensitive to the location of the camera relative to the eye. Therefore, even small movements of the camera (called 'slippage') can produce errors in the eye orientation estimation and consequently large errors in the gaze target estimation (especially for targets located far from the eye).

US publication 2016/0320837 (now U.S. Pat. No. 10,248, 194) assigned to MIT, combines images of retinal retroreflections (RR) to create a digital (or reconstructed) image of a person's retina. An RR is not an image of a portion of the retina. A known direction of gaze of the eye can be used to determine the precise position of each RR to enable image reconstruction. The MIT publication describes capturing a sequence of RRs and comparing this sequence to a database of known sequences of RRs, to calculate a direction of gaze. The MIT publication itself explains that calculating gaze direction from only a single RR is difficult, because any individual RR may result from more than one gaze direction. Thus, this method is not suitable and is not used for real-time gaze tracking.

US publication 2017/0188822 assigned to the University of Rochester describes a method used to compensate for a motion of a subject's eye during a scanning laser ophthalmoscopy procedure. This publication deals with cases where the subject is constantly looking at the same gaze target. The method described in this publication does not calculate the actual orientation of the eye or the actual direction of gaze of the person, or changes to such (e.g. in angles) and is not suitable for determining gaze direction of an unknown gaze target.

To date, accurate real-time gaze tracking remains a challenging task.

SUMMARY

Embodiments of the invention provide a system and method for gaze tracking using a camera. The camera is typically positioned such that at least part of the retina of the eye is imaged, and a change in orientation of the eye may be calculated based on comparison of two images. Direction of gaze (and/or other information such as gaze target and/or ray of gaze) is determined, according to embodiments of the invention, based on the calculated change in orientation.

In embodiments of the invention, a person's direction of gaze in an image associated with an unknown direction of gaze can be determined based on another image of the person's retina which is associated with a known direction of gaze. In some embodiments, a direction of gaze is determined by finding a spatial transformation between an image of the retina at a known direction of gaze and a matching image of the retina at an unknown direction of gaze. In other embodiments, a direction of gaze is determined by calculating a location of the person's fovea based on the images of the retina. As such, gaze tracking, according to embodiments of the invention, is less sensitive to changes of the position of the camera relative to the eye. Therefore, systems and methods according to embodiments of the invention are less prone to errors due to small movements of the camera relative to the user's eye.

A system according to embodiments of the invention includes a retinal camera which consists of an image sensor to capture images of a person's eye and a camera lens configured to focus light originating from the person's retina on the image sensor. The system also includes a light source producing light emanating from a location near the retinal camera and a processor to calculate a change in orientation of the person's eye between two images captured by the image sensor.

The processor may further calculate one or more of: an orientation of the person's eye, a direction of gaze of the person, a gaze target and a ray of gaze, based on the change in orientation of the person's eye between the two images.

The system may further include a beam splitter (e.g., a polarizing beam splitter) configured to direct light from the light source to the person's eye. The light source may be a polarized light source and the system may also include a polarizer configured to block light originating from the light source and reflected through specular reflection.

Methods, according to embodiments of the invention, are used to efficiently match retina images with reference images to provide effective and accurate gaze tracking and for other applications, such as biometric identification and medical applications.

BRIEF DESCRIPTION OF THE FIGURES

The invention will now be described in relation to certain examples and embodiments with reference to the following illustrative figures so that it may be more fully understood. In the drawings.

DETAILED DESCRIPTION

Figure 1A:
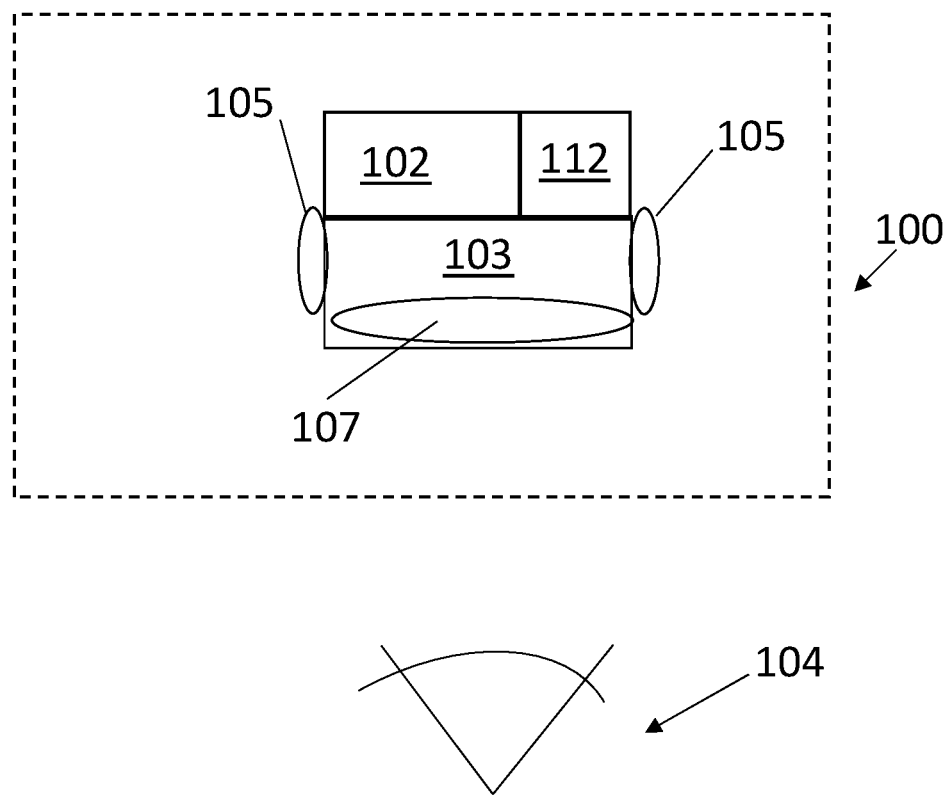
FIGS. 1A, 1B and 1C schematically illustrate systems operable, according to embodiments of the invention.

As described above, when a person is gazing at a target, light entering the person's eye through the pupil falls on the inner coating of the eyeball, the retina. The part of the image that falls on the center of the fovea is the image of the gaze target.

A ray of sight corresponding to the person's gaze (also termed "ray of gaze" or "gaze ray") includes the origin of the ray and its direction. The origin of the ray can be assumed to be at the optical center of the person's lens (hereinafter 'lens center') whereas the direction of the ray is determined by the line connecting the origin of the ray and the gaze target. Each of a person's two eyes has its own ray of gaze and under normal conditions the two meet at the same gaze target.

The position of the lens center may be estimated using known methods, such as by identifying the center of the pupil in an image and measuring the size of the iris in the image.

The direction of the ray of gaze is derived from the orientation of the eye. When a gaze target is near the eye (e.g., about 30 cm or less), the origin of the ray of gaze and its direction are both important in obtaining angular accuracy when calculating the gaze target. However, when the gaze target is located further away from the eye, the direction of the ray becomes significantly more important than the origin of the ray, in obtaining angular accuracy when calculating the gaze target. At the extreme, when gazing at infinity, the origin has no effect on angular accuracy.

As any rigid object in a 3D space, a complete description of the pose of the eye has six degrees of freedom; three positional degrees of freedom (e.g. x, y, z) relating to translational movements, and three orientational degrees of freedom (e.g. yaw, pitch, roll) relating to rotations. Orientation and position of the eye may be measured in any frame of reference. Typically, in embodiments of the invention, orientation and position of the eye are measured in a camera's frame of reference. Thus, throughout this description, a camera frame of reference is meant even if no frame of reference is mentioned.

Embodiments of the invention provide a novel solution for finding the orientation of the eye from which the direction of gaze and/or the gaze target and/or the ray of gaze can be derived.

Systems and methods for determining orientation of an eye of a person, according to embodiments of the invention, are exemplified below.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "analyzing", "processing," "computing," "calculating," "determining," "detecting", "identifying", "creating", "producing", "predicting", "finding", "trying", "choosing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Unless otherwise stated, these terms refer to automatic action of a processor, independent of and without any actions of a human operator.

In one embodiment, a system 100, which is schematically illustrated in FIG. 1A, includes one or more camera(s) 103 configured to obtain images of at least a portion of one or both of a person's eye(s) 104. Typically, camera 103 is a retinal camera, which obtains an image of a portion of the person's retina, via the pupil of the eye, with minimal interference or limitation of the person's field of view (FoV). For example, the camera 103 may be located at the periphery of a person's eye (e.g., below, above or at one side of the eye) a couple of centimeters from the eye. In one embodiment the camera 103 is located less than 10 centimeters from the eye. For example, the camera may be located 2 or 3 centimeters from the eye. In other embodiments the camera is located more than 10 cm from the eye, e.g., a few tens of centimeters or even several meters from the eye.

Camera 103 may include a CCD or CMOS or other appropriate image sensor and an optical system which may include, for example, lens 107. Additional optics such as mirrors, filters, beam splitters and polarizers, may be included in the system. In other embodiments camera 103 may include a standard camera provided, for example, with mobile devices such as smartphones or tablets.

Camera 103 images the retina with a suitable lens 107, converting rays of light from a particular point of the retina to a pixel on the camera sensor. For example, in one embodiment, the camera is focused at infinity. If the eye is focused at infinity, as well, rays of light originating from a particular point of the retina exit the eye as a collimated beam (since, in the other direction, the eye is focusing incoming collimated beams to a point on the retina). Each collimated beam is focused by the camera to a particular pixel on the camera sensor depending on the direction of the beam. If the camera or the eye are not focused at infinity, a sharp enough image of the retina could still be formed, depending on the camera's optical parameters, and the exact focus of each of the camera and the eye.

Since the eye is not a perfect lens, the wavefront of rays exiting the eye is distorted from that of a perfect lens, mainly by the eye lens and cornea. This distortion differs from person to person and also depends on the angle, relative to the optical axis of the eye, of the exiting wavefront. The distortion may reduce the sharpness of the image of the retina captured by camera 103. In some embodiments, camera 103 may include a lens 107, which is optically designed to correct for aberrations to the light originating from the person's retina, aberration caused by the eye. In other embodiments the system includes a Spatial Light Modulator designed to correct the aberrations to the light originating from the person's retina by distortion of a typical eye, or of a specific person's eye, and to correct the distortion expected at the angle of the camera position relative to the eye. In other embodiments aberrations may be corrected by using appropriate software.

In some embodiments camera 103 may include a lens 107 with a wide depth of field or having an adjustable focus. In some embodiments lens 107 may be a multi-element lens.

A processor 102 is in communication with camera 103 to receive image data from the camera 103 and to calculate a change in orientation of an eye of the person, and possibly determine the person's direction of gaze, based on the received image data. Image data may include data such as pixel values that represent the intensity of light reflected from a person's retina, as well as partial or full images or videos of the retina or portions of the retina.

Often, images obtained by camera 103 may include different parts of the eye and person's face (e.g., iris, reflections on the cornea, sclera, eyelid and skin) in addition to the retina, which is visible through the pupil. In some embodiments processor 102 may perform segmentation on the image to separate the pupil (through which the retina is visible) from the other parts of the person's eye or face. For example, a Convolutional Neural network (CNN), such as UNet, can be used to perform segmentation of the pupil from the image. This CNN can be trained on images where the pupil was manually marked.

The eye returns light back in approximately the same direction it entered. Therefore, embodiments of the invention provide a well-positioned light source in order to avoid cases where the light from the light source doesn't return to the camera, causing the retina to appear too dark to be properly imaged. Some embodiments of the invention include a camera, having an accompanying light source 105. Thus, system 100 may include one or more light source(s) 105 configured to illuminate the person's eye. Light source 105 may include one or multiple illumination sources and may be arranged, for example, as a circular array of LEDs surrounding the camera 103 and/or lens 107. Light source 105 may illuminate at a wavelength which is undetected by a human eye (and therefore unobtrusive), for example, light source 105 may include an IR LED or other appropriate IR illumination source. The wavelength of the light source (e.g., the wavelength of each individual LED in the light source), may be chosen so as to maximize the contrast of features in the retina and to obtain an image rich with detail.

In some embodiments a miniature light source may be positioned in close proximity to the camera lens 107, e.g., in front of the lens, on the camera sensor (behind the lens) or inside the lens.

Figure 1B:
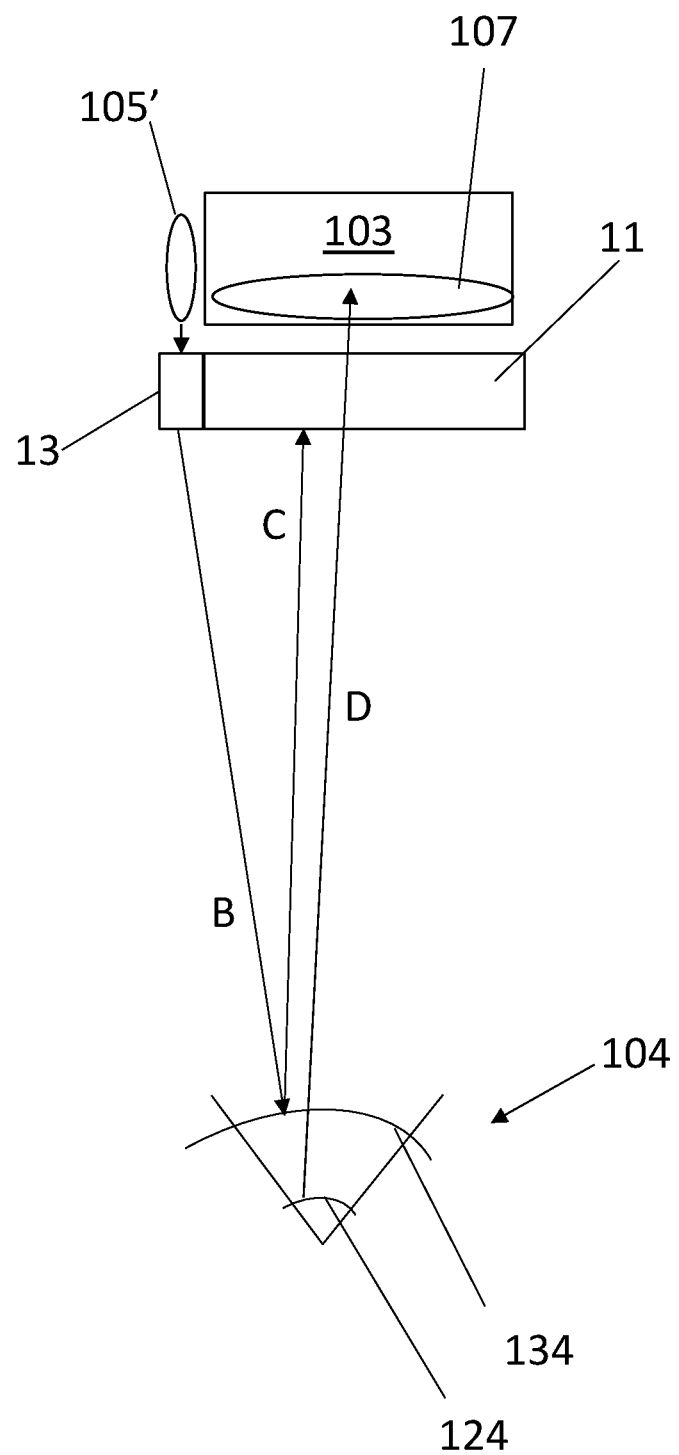

In one embodiment, an example of which is schematically illustrated in FIG. 1B, an LED 105' positioned near lens 107 of camera 103, illuminates eye 104.

Glint, which may sometimes be caused by specular reflection of light from the anterior segment of the eye 134 (which is mostly smooth and shiny), can obstruct images of the retina 124, reducing their usefulness. Embodiments of the invention provide a method for obtaining an image of a person's eye with reduced glint, by using polarized light. In one embodiment, a polarizing filter 13 is applied to LED 105' to provide polarized light. In another embodiment the light source is a laser, which is naturally polarized.

Light polarized in a certain direction (whether linear or circular) and directed at the eye (arrow B), will be reflected back from the anterior segment of the eye 134 through specular reflection (arrow C), which mostly maintains polarization (or in the case of circular polarization—reversing it). However, the light reflected from the retina 124 will be reflected back through diffuse reflection (arrow D), which randomizes polarization. Thus, using a filter 11 that blocks light in the original polarization (or reverse polarization, if circular), will enable receiving the light reflected from the retina 124 but will block most of the light reflected from the anterior segment of the eye 134, therefore substantially removing glint from the images of the eye.

Figure 1C:
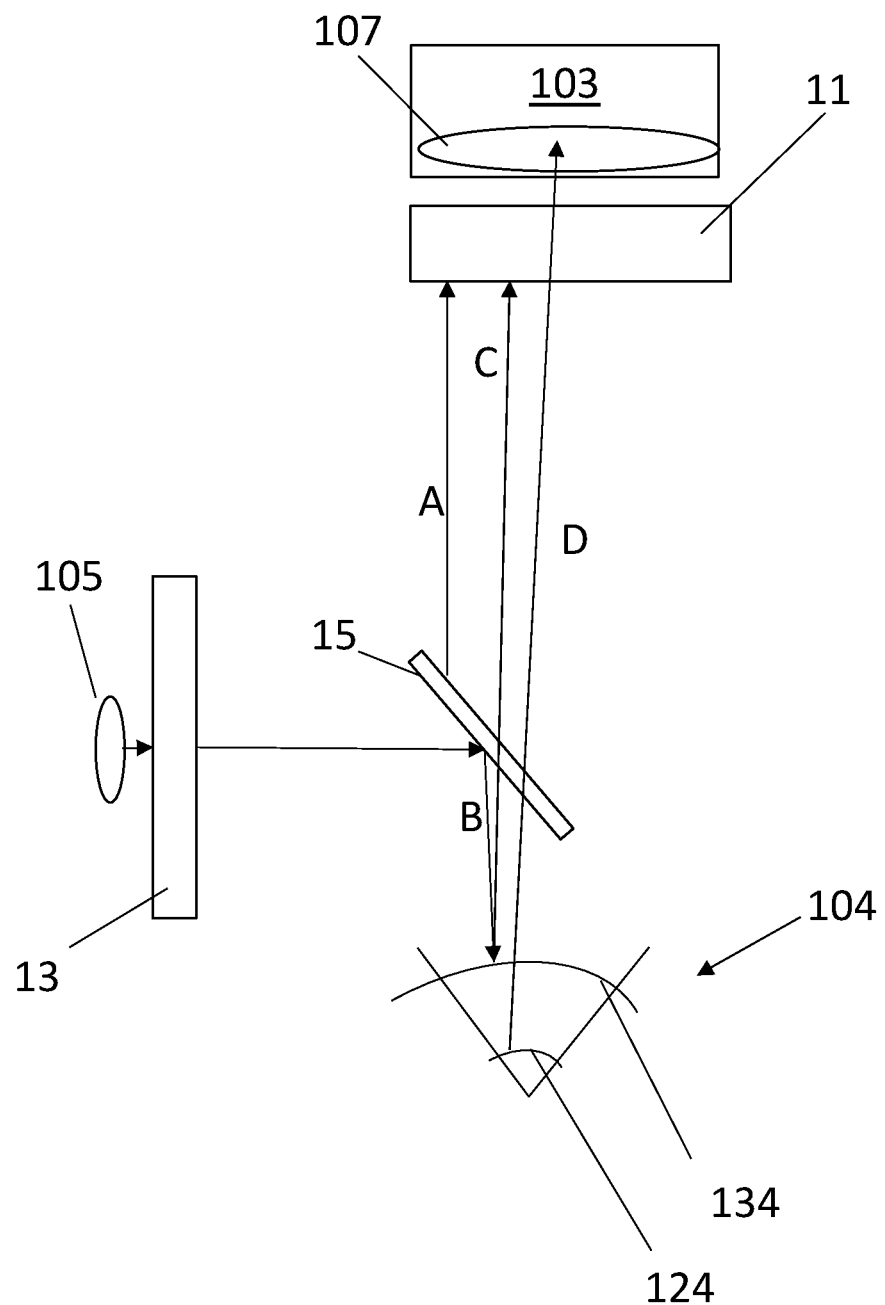

In another embodiment, an example of which is schematically illustrated in FIG. 1C, in order to achieve an effect of the light appearing to be emanating from the camera lens, a beam splitter 15 may be included in system 100. A beam splitter can align the light from light source 105 with the camera's lens 107, even if the light source 105 is not in physical proximity to the camera's lens 107.

When using a beam splitter 15 to generate a light beam that seems to be emanating from within or close to the camera lens 107, some of the light may be reflected back from the beam splitter (arrow A) and may cause a glare that can obstruct the view of the retina. The glare from the beam splitter can be reduced by using polarized light (e.g., by applying a polarizing filter 13 to light source 105) and a polarizing filter 11 in front of the camera lens 107. Using polarized light to reduce the glare from the beam splitter 15 will also reduce the glint from the eye, since the light reflected from the outer parts of the eye (arrow C) is polarized in the same direction as the light reflected from the beam splitter directly to the camera (arrow A), and both are polarized orthogonally to the polarizing filter 11 on or in front of the camera lens 107.

Thus, in one embodiment, light source 105 includes a filter (e.g., polarizing filter 13) or an optical component to produce light in a certain polarization for illuminating a person's eye 104, or, is a naturally polarized source such as a laser. In this embodiment, system 100 includes a polarizing filter 11 that blocks light of the polarization that is reflected back from the anterior segment of the eye 134 to the camera 103 (arrow C) but will allow the diffuse reflection from the retina 124 (arrow D) to pass through to the camera 103, thus obtaining an image of the retina with less obstruction. For example, the polarizing filter 11 may allow only light perpendicular to the polarization of light source 105.

In some embodiments system 100 includes a polarizing beam splitter. Using a polarizing beam splitter, possibly in conjunction with additional polarizers, can provide similar benefits.

In embodiments where the camera 103 is placed far from the eye plane of focus (e.g. the camera may be positioned 3 cm from the eye while the eye may be focused at a screen positioned 70 cm from the eye), light source 105 may be placed at very close proximity to the camera lens 107, e.g., as a ring around the lens, rather than appear to be coming from the camera lens 107. This is still effective since the image of light source 105 on the retina will be blurred, allowing some of the light to return in a slightly different direction and reach the camera.

Processor 102, which may be locally embedded or remote, may include, for example, one or more processing units including a central processing unit (CPU), a graphics processing unit (GPU), a digital signal processor (DSP), a field-programmable gate array (FPGA), a microprocessor, a controller, a chip, a microchip, an integrated circuit (IC), or any other suitable multi-purpose or specific processing or controlling unit.

Processor 102 is typically in communication with a memory unit 112, which may store at least part of the image data received from camera(s) 103. Memory unit 112 may be locally embedded or remote. Memory unit 112 may include, for example, a random access memory (RAM), a dynamic RAM (DRAM), a flash memory, a volatile memory, a non-volatile memory, a cache memory, a buffer, a short term memory unit, a long term memory unit, or other suitable memory units or storage units.

In some embodiments the memory unit 112 stores executable instructions that, when executed by processor 102, facilitate performance of operations of processor 102, as described herein.

The processor 102 may be in communication with the light source 105 to control the light source 105. In one example, portions of the light source 105 (e.g., different LEDs of a circular array) may be controlled individually by processor 102. For example, the intensity and/or timing of illumination of portions of the light source (e.g., every LED in the array) can be individually controlled, e.g., to be synchronized with operation of camera 103. Different LEDs, having different wavelengths can be turned on or off to obtain different wavelength illumination. In one example, the amount of light emitted by light source 105 can be adjusted by processor 102 based on the brightness of the captured image. In another example, light source 105 is controlled to emit different wavelength lights such that different frames can capture the retina at different wavelengths, and thereby capture more detail. In yet another example, light source 105 can be synchronized with the camera shutter. In some embodiments, short bursts of very bright light can be emitted by light source 105 to prevent motion blur, rolling shutter effect, or reduce overall power consumption. Typically, such short bursts are emitted at a frequency that is higher than human perception (e.g. 120 Hz) so as not to disturb the person.

In one embodiment, the system 100 includes one or more mirror(s). In one embodiment camera 103 is directed at the mirror. The mirror and the camera 103 may be placed such that light reflected from the eye hits the mirror and is reflected to the camera 103. This allows the camera to be positioned at the periphery of the eye without blocking the user's FoV.

In another embodiment, the camera is directed at several small mirrors. The mirrors and the camera are placed such that light reflected from the eye hits the mirrors and is reflected to the camera. The position of each mirror determines the camera viewpoint into the pupil. The use of several mirrors allows to capture several viewpoints into the eye at the same time, which offers a larger view of the retina. Thus, in some embodiments system 100 includes a plurality of mirrors designed and arranged to enable simultaneously capturing several viewpoints of the person's retina.

In another embodiment the system 100 includes a concave mirror. The concave mirror and the camera are placed such that light reflected from the eye hits the mirror and is reflected to the camera. Using a concave mirror has an effect similar to placing the camera closer to the eye, resulting in an image with a larger FoV of the retina.

In some embodiments, the system 100 includes one or more mirrors designed to reflect light at predetermined wavelengths. For example, the system may include one or more IR mirrors that are transparent at visible light. Such mirrors may be placed in front of the eye without interfering with the person's view. IR light from a light source (e.g., light source 105) adjacent to the camera, directed at the mirror, may be reflected into the eye. The light is reflected from the retina back to the mirror from which it is reflected once again back to the camera. Light reflected to the camera exits the eye at a small angle relative to the eye's optical axis, where optical performance is typically better, resulting in a sharper image. Thus, such a setup allows the camera to capture clearer images of the retina without blocking the person's FoV.

In an alternative embodiment, camera 103 includes a photosensor and light source 105 includes a laser scanner (e.g. MEMS laser scanner). An image of the eye and retina may be obtained using a MEMS laser scanner located near a photosensor (proximity is needed so that the photosensor can sense light returning from the retina through the pupil). A laser from the laser scanner passes through a lens or other optical element located in front of the laser scanner and designed to cause the laser to focus to a small area on the retina, in order to create a sharp image of small retinal details. The laser rapidly traverses the eye, each instant illuminating a different point. The photosensor senses the light returning from the eye (and from the retina, through the pupil), and by associating the sensed value with the direction of the laser at that instant, an image can be created. This image is then processed as described herein.

Thus, in one embodiment, system 100 includes a laser scanner located near a photosensor and directed towards a person's eye. The laser scanner is designed to emit a laser in a plurality of directions. The photosensor senses values of light returning from the retina of the person's eye. Processor 102 creates an image of the retina from the values sensed by the photosensor at each direction of the plurality of directions of the laser scanner and calculates a change in orientation of the eye between two images created by the processor.

In some embodiments, the camera 103 may be located at a significant distance from the eye (e.g., a few tens of centimeters or a few meters). At this distance, the portion of the retina visible to the camera may be too small to obtain enough details for a reliable comparison of images. In this case, a camera with a larger lens (and/or concave mirror, and/or waveguide) may be used to capture a wider range of angles of rays emanating from the retina through the pupil.

Other optional methods for obtaining images when the camera is at a large distance from the eye, are detailed further below.

In another embodiment, the system 100 includes a waveguide configured to guide light from the person's retina towards the camera 103. In some embodiments, near-eye AR or VR optical systems (such as the Lumus™ DK-Vision, Microsoft™ Hololens, or Magic Leap One™) use waveguide technology to project a virtual image to a user's eye while enabling to transmit external light to the eye so that a user can see both the virtual image and the real-world scene. Embodiments of the invention provide gaze tracking compatible with such an AR or VR optical system. For example, a light source 105 can be located (typically outside of the user's FoV) such that light is transmitted via the waveguide to the user's eye. Light being reflected back from the user's retina will be transmitted, via the waveguide, to a camera, such as camera 103, to provide an image of the retina to processor 102 to calculate a change in orientation of the eye and optionally the direction of gaze of the user, based on the images of the retina, as described herein. The light reflected back from the retina will be incident on the waveguide at the same location where the light from light source 105 was directed to the eye. From there, the light will be propagated through the waveguide to the camera 103. When using a waveguide, rays coming at mirroring angles will merge. Therefore, light source 105 can be placed at a mirror angle to camera 103 to achieve an effect as if the light source is illuminating from near the camera. Thus, the light source 105 and camera 103 do not have to be physically near each other when providing gaze tracking to an AR or VR system.

Retinal images acquired through waveguides of a near-eye AR or VR optical systems typically contain a larger portion of the retina. Also, the retinal features may appear darker relative to other obstructions that may appear at the same region of the image. For example, due to the nature of waveguide imaging, and the way it handles non-collimated light, blurry images of regions of the outer part of the eye may overlay the weak but sharp image of retinal features. In some embodiments, cameras with a high bit-depth may be used to generate an image where these weak but sharp retinal features can be extracted, e.g., by using a high pass filter on the image.

In some embodiments, an optical element may be used in front of light source 105 in order to collimate the light beam before the waveguide. The collimated light will appear to the user as if emanating from a distant point source and will be focused by the eye to a small region on the retina. This small region will appear brighter in the image acquired by the camera, thus improving its quality.

In some embodiments processor 102 may be in communication with a user interface device including a display, such as a monitor or screen, for displaying images, instructions and/or notifications to a user (e.g., via text or other content displayed on the monitor). In other examples, processor 102 may be in communication with a storage device such as a server, including for example, volatile and/or non-volatile storage media, such as a hard disk drive (HDD) or solid-state drive (SSD). The storage device, which may be connected locally or remotely, e.g., in the cloud, may store and allow processor 102 access to databases of reference images, maps linking reference images to known directions of gaze and/or to locations of the fovea and more, as further described herein.

Components of system 100 may be in wired or wireless communication and may include suitable ports and/or network hubs.

In one embodiment, system 100 includes camera 103 to obtain a reference image, which includes at least a portion of the person's retina associated with a known orientation of the person's eye and/or a known direction of gaze of the person and/or a known gaze target and/or a known ray of gaze, and an input image, which includes at least a portion of the person's retina associated with an unknown orientation of the person's eye and/or an unknown direction of gaze of the person and/or an unknown gaze target and/or an unknown ray of gaze. To simplify, and because each of the parameters (orientation of eye, direction of gaze, gaze target and ray of gaze), are related, when "direction of gaze" is referred to herein, the other parameters are included.

Processor 102, which is in communication with the camera 103 determines the person's direction of gaze in the input image based on the reference image, the known direction of gaze and the input image.

In one embodiment processor 102 receives an input image and compares the input image to a reference image, to find a spatial transformation (e.g., translation and/or rotation) of the input image relative to the reference image. Typically, a transformation that optimally matches or overlays the retinal features of the reference image on the retinal features of the input image, is found. A change in orientation of the person's eye, which corresponds to the spatial transformation is then calculated. The direction of gaze associated with the input image can then be determined based on the calculated transformation (or based on the change in eye orientation). A signal based on the change in orientation and/or based on the person's direction of gaze associated with the input image, may be output by processor 102.

In some embodiments, the calculated transformation is converted to a corresponding spherical rotation and the direction of gaze associated with the input image is determined by using the spherical rotation to rotate the known direction of gaze associated with the reference image.

A spherical rotation is defined as a linear map of 3D space onto itself that preserves lengths and chirality. I.e., it is equivalent to a 3×3 real matrix R such that $RR^t=1$ and $\det(R)=1$.

The transformation of the reference image relative to the input image is the inverse of the transformation of the input image relative to the reference image. Mutatis mutandis, the direction of gaze associated with the input image may also be determined based on the transformation of the reference image relative to the input image. Thus, the term "transformation of the input image relative to the reference image" or similar terms used herein, are meant to include also transformation of the reference image relative to the input image.

Images of a person's eye may include the fovea and the retina, mainly, features of the retina, such as, patterns of blood vessels that supply the retina.

Throughout this description, calculations of eye orientation or gaze direction are explained with reference to a pixel of the fovea. The term "pixel of fovea" or "location of fovea" or similar terms herein may refer to an actual pixel, if the fovea is visible, or to a theoretical pixel, as described below, if the fovea is not visible. The pixel is the camera's projection of the gaze direction vector on the camera sensor. A theoretical (or calculated) location of the fovea refers to a theoretical pixel that is outside the visible parts of the retina in the image, and can even be (and usually is) outside the camera FoV (i.e. the location of the theoretical pixel is outside the image sensor). The calculated (theoretical) pixel location of the fovea corresponds to an angle in the camera frame of reference. A person's direction of gaze can be calculated from this angle. For an image associated with a known gaze direction, the pixel location of the fovea is calculated from this angle.

Reference to the pixel of the fovea is done for an illustrative explanation of the relationship between direction of gaze and retinal images. However, spherical rotations and other spatial transformations, according to embodiments of the invention, can be applied directly to the orientation of the eye or to the gaze direction (as a 3D vector) without first projecting it to the fovea pixel (whether actual or theoretical).

There is a one-to-one map between the location of retinal features in an image, and the eye's orientation relative to the camera capturing the image. This map is a function of the eye orientation and the camera properties. It is independent of the position of the eye relative to the camera. In way of explanation, imagine both the eye and the camera are focused at infinity. Light reflected from the retina is projected to space as an angular pattern. That is, each point on the retina corresponds to a collimated beam in a particular orientation. If the orientation of the eye in space is fixed, so is the orientation of each collimated beam, regardless of the spatial position of the eye. In turn, the camera focuses each collimated beam to a particular pixel on the camera sensor, depending on the orientation of the beam. Therefore, for each orientation of the eye, each retinal feature corresponds to a collimated beam at a corresponding orientation, which is focused by the camera to a particular location in the image.

In one embodiment, the direction of the beam originating from the fovea can be calculated from the pixel at which the fovea appears in an image. For example, in a pinhole camera with focal length f and optical center at pixel (0,0), a fovea location, or theoretical location, (x, y) on the camera sensor corresponds to a beam orientation described by the unit vector $$\frac{(-x, -y, f)}{\sqrt{(x^2 + y^2 + f^2)}}.$$

In one embodiment, a direction of gaze can be determined from images of an eye, e.g., retina of the eye, based on calculated locations of a person's fovea. In this example, processor 102 receives from camera 103 a reference image, which is obtained while a person is looking in a known direction. The location of the fovea on the camera sensor for each reference image can be determined since each direction of gaze uniquely corresponds to a known location of the fovea. In other embodiments, as discussed above, the location of the fovea (actual or theoretical) corresponds to an angle in the camera frame of reference. A person's direction of gaze can be calculated from this angle. Processor 102 compares an input image of the person's retina, which is obtained from camera 103 while tracking the (unknown) direction of gaze of a person, to a map of reference images. The map links portions of the person's retina, as they appear in the camera images, to known locations of the person's fovea. Processor 102 may identify one or more reference images correlating to or matching the input image and may then determine the spatial transformation (e.g., translation and/or rotation) of the input image in relation to a corresponding reference image(s). The determined translation and/or rotation can be used to calculate the location of the person's fovea in the input image, to obtain a calculated location of fovea. The fovea's calculated (theoretical) location corresponds to a theoretical angle the camera would have mapped to a theoretical larger sensor. This theoretical angle is the person's angle of gaze in terms of the camera's axes.

The person's direction of gaze associated with the input image can thus be determined based on the calculated location of the person's fovea. Processor 102 may output a signal based on the determined direction of gaze.

In some embodiments the fovea can be identified directly in an image where it is visible (e.g., when the person is gazing at or near the camera). For example, the fovea can be identified based on a different color/brightness of the fovea compared with the retina. An image in which the fovea is identified can be stitched to a panorama (as further described below) providing a panorama image which includes the fovea.

Figure 2A:
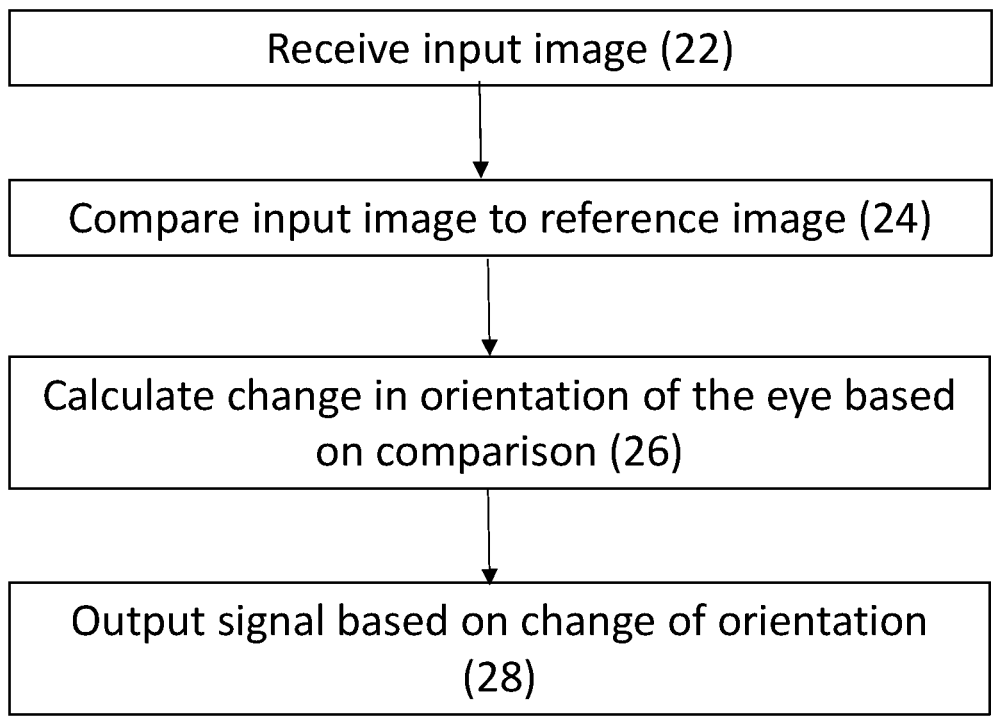
FIGS. 2A and 2B schematically illustrate methods for calculating a change in orientation of an eye, from which a direction of gaze of a person can be determined, according to embodiments of the invention.

In one example which is schematically illustrated in FIG. 2A, a method for determining a direction of gaze of a person, which may be carried out by processor 102, includes receiving an input image which includes at least a portion of the person's retina (step 22). In some embodiments, the input image is associated with an unknown direction of gaze. The input image is compared to a reference image (step 24), which includes at least a portion of the person's retina. Typically, the reference image is associated with a known direction of gaze. Comparing the reference image to the input image may include, for example, finding a spatial transformation (e.g. a rigid transformation such as translation and/or rotation) between the input image and the reference image. A change in orientation of the person's eye, which corresponds to the spatial transformation, is then calculated (step 26) and a signal is outputted based on the change in orientation (step 28).

Methods according to embodiments of the invention may proceed using optimal calculations (e.g., assuming the lens of the eye is a perfect lens and/or assuming the camera is a pinhole camera). However, since neither are perfect, in some embodiments, the obtained images (e.g., input and reference images) are processed to correct distortions (e.g., geometrical distortions), prior to finding the spatial transformation between the input image and reference image. The processing, in one embodiment, may include geometrically undistorting the input and reference images. Thus, processor 102 may geometrically undistort the input image to obtain an undistorted input image and may obtain a comparison of the undistorted input image with an undistorted reference image (e.g., in step 24). Calculations for geometrically undistorting (correcting image distortions) are described below. Additionally, known software can be used for the processing of images to obtain undistorted images.

The signal outputted in step 28 may be a signal to indicate a direction of gaze or, for example, to indicate a change in direction of gaze. In some embodiments the outputted signal may be used to control a device, as further exemplified below.

Figure 2B:
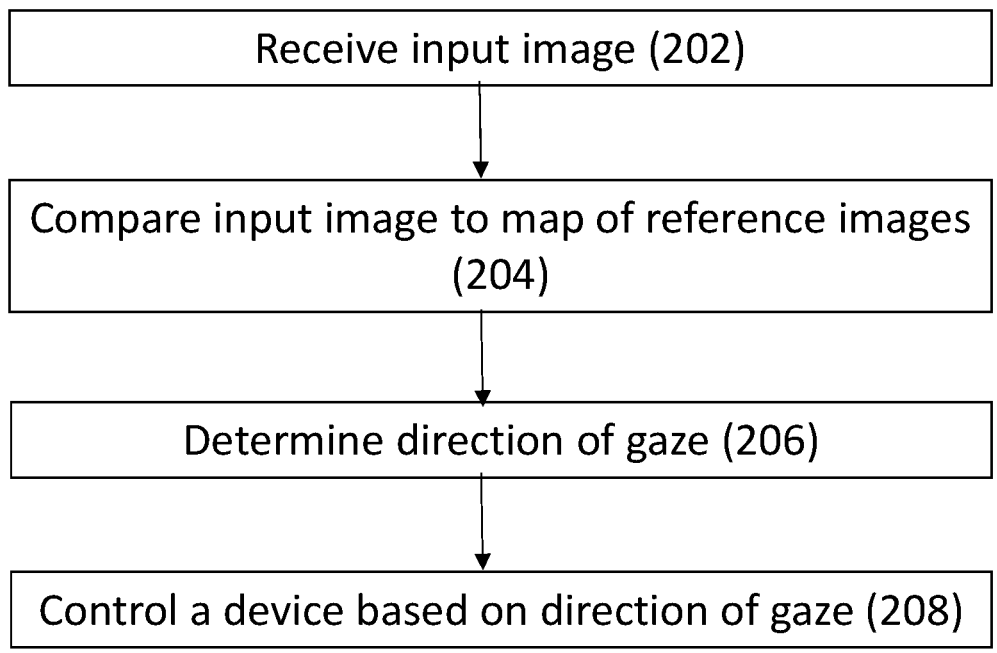

In another embodiment, which is schematically illustrated in FIG. 2B, a method for determining a direction of gaze of a person includes receiving an input image of at least a portion of the person's eye, e.g., a portion of the retina (step 202) and comparing the input image to a map of reference images, which are images of portions of the person's eye that are linked to known directions of gaze (step 204). The person's direction of gaze associated with the input image can be determined based on the comparison (step 206). In some embodiments a signal may be output based on the person's direction of gaze. The signal may be used to indicate the determined direction of gaze or, for example, to indicate a change in direction of gaze. In some embodiments the outputted signal may be used to control a device. Thus, in some embodiments, a device is controlled based on the person's direction of gaze (step 208).

Reference images typically include a portion of the retina but do not include the fovea. Thus, the known direction of gaze which is linked to each reference image may be outside the field of view of the camera. Namely, projecting the gaze direction onto the image sensor would result in a theoretical pixel outside of the image frame.

A plurality of transformed (e.g., translated and rotated) copies of the input image may be compared to the reference image using, for example, a Pearson correlation coefficient between the pixel values of each image, or a similar function.

Each transformed copy is transformed differently (e.g., has a different translation and/or rotation). The copy with the highest Pearson correlation to the reference image may be used to determine the transformation (e.g., translation and/or rotation) of the input image relative to the reference image and the corresponding change in the orientation of the person's eye.

In some cases, applying Pearson correlation to two images can result in relatively high values even if the two images are not similar. This happens because each image has high spatial autocorrelation (i.e., near pixels tend to have similar values). This can substantially increase the probability that areas on two not similar images will be correlated by chance. To reduce this effect of false positives, Pearson correlation can be applied only to sparse descriptions of the image, which have lower autocorrelation. A sparse description of retina images may include, for example, the position of extremal points and sharp edges in the image.

Thus, in some embodiments, comparison of retina images, (e.g., when using Pearson correlation) is done by using a sparse description of the images.

As described in step 208 above, a device may be controlled based on the person's direction of gaze. For example, a user interface device may be updated to indicate the person's direction of gaze when there is a change of direction. In another embodiment another device may be controlled to issue a warning or other signal (e.g., an audio or visual signal) based on the person's direction of gaze.

In some embodiments, devices controlled based on a person's direction of gaze may include industrial machines, devices used in sailing, aviation or driving, devices used in medical procedures, devices used in advertising, devices using virtual or augmented reality, computer games, devices used in entertainment, etc. Alternatively or in addition, a device for biometric user identification may be controlled based on the person's direction of gaze, according to embodiments of the invention.

In another example, embodiments of the invention include devices using virtual reality (VR) and/or augmented reality (AR) (that can be used in a variety of applications such as gaming, sailing, aviation, driving, advertising, entertainment, etc.). A person's direction of gaze, determined according to embodiments of the invention, can be used to control VR/AR devices.

In one embodiment, a device used in a medical procedure may include components described in FIG. 1. For example, a system may include a retinal camera consisting of an image sensor to capture images of a person's retina, each image associated with a different direction of gaze of the person. The system may also include a processor to find spatial transformations between the images and to stitch together the images based on the spatial transformations, to create a panorama image of the person's retina.

In some cases, a person is requested to gaze at extreme angles, when obtaining the retinal images of the person's retina, such that these images are associated with extreme directions of gaze of the person and enable obtaining a wider view of the retina.

The processor can cause the panorama image to be displayed, e.g., to be viewed by a professional.

In some embodiments the processor can run a machine learning model to predict a health state of the person's eye based on the panorama image, the machine learning model trained on panorama images of retinas of eyes in different health states.

Viewing a panorama according to embodiments of the invention, provides a non-invasive and patient-friendly medical procedure (e.g., a procedure of examining a person's optic nerve or other features of the retina), which to-date, includes administering pupil dilating eye drops and shining a bright light into the person's eye, and may produce a narrower view into the retina. Additionally, since a panorama according to embodiments of the invention may be obtained using simple and cheap hardware, this non-invasive medical procedure can be used in a home setting and/or in remote areas.

In some embodiments, which are also schematically illustrated in FIGS. 3A and 3B below, a device for biometric user identification or authentication, may include components described in FIG. 1.

In one example, a device for biometric identification includes one or more cameras to obtain a reference image and an identification image. The reference image includes at least a portion of the person's retina. Some or all of the reference images are obtained at known directions of gaze. In some embodiments, the reference images are linked to known locations of the person's fovea in the image, or to a theoretical pixel of the fovea. The identification image includes at least a portion of the person's retina at the known direction of gaze or at a different known direction of gaze.

In some embodiments the device for biometric user identification includes two cameras, each camera arranged to obtain a reference image and an identification image of each eye of the person. In some embodiments, two or more cameras are arranged to obtain reference images and identification images of the same eye. Reference images and identification images of different eyes of the person may also be obtained by a single camera that has both eyes in its field of view, either directly or through mirrors or waveguides.

In one embodiment, the device for biometric user identification includes a processor in communication with the one or more camera and with a storage for maintaining reference images linked to peoples' identities. The processor compares an identification image of a person to the reference images and determines the person's identity based on the comparison.

In one embodiment, the comparison is done by spatially transforming (e.g., rigidly transforming) the identification image one or more times and calculating the strength of correlation between the transformed identification image and the reference image. The processor then determines the person's identity based on the strength of correlation.

For example, the strength of correlation may be determined by the Pearson correlation coefficient obtained when comparing transformed identification images to reference images. In some embodiments a maximal Pearson coefficient is calculated and the strength of correlation may be measured by the likelihood of a retina of a random person achieving this maximal coefficient. Such a likelihood or probability could be calculated, for example, by using a database of images of retinas of many people. Random persons are checked against this database and a probability can be calculated from the number of positive (but false) identifications of the random persons. Alternatively, a measure of the strength of the correlation (e.g. Pearson correlation coefficient) can be calculated for each of the random persons, and a probability distribution function (pdf) of that measure among random people can be estimated from these samples. The probability of a false match would then be the integral of that pdf from the correlation strength of the identification image to infinity.

Figure 3A:
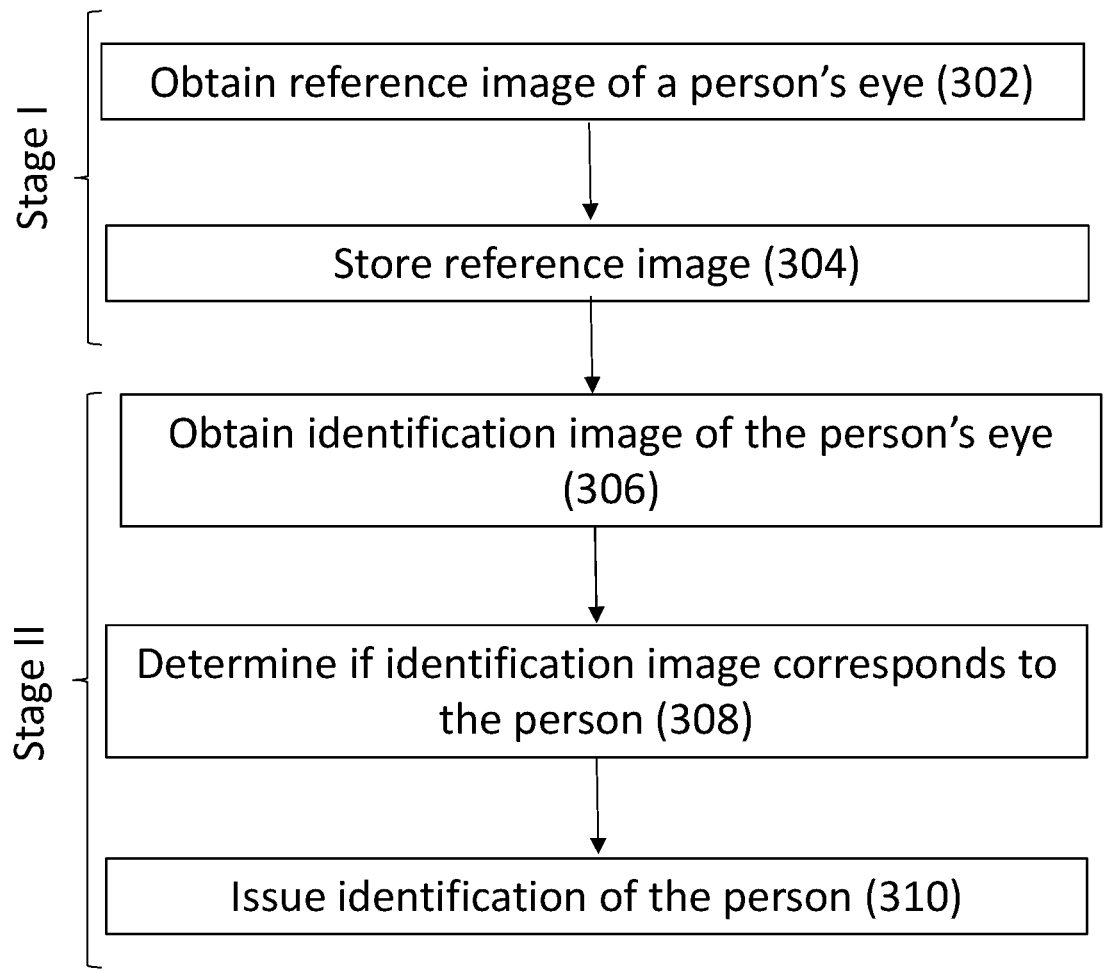
FIGS. 3A and 3B schematically illustrate examples of methods for biometric identification, according to embodiments of the invention.

One example of controlling a device for biometric user identification, based on a determined direction of gaze, according to embodiments of the invention, is schematically illustrated in FIG. 3A.

In an initial stage (stage I) a reference image of a person's eye is obtained (step 302). For example, a reference image may be obtained by camera 103 that is located less than 10 centimeters from the person's eye, with minimal interference or limitation of the person's field of view.

In some embodiments, the reference image includes at least a portion of the person's retina while the person is looking at a known direction X. The obtained reference image is stored (step 304), e.g., in a user's identity database. Typically, a plurality of reference images of a single person (obtained at different known directions) and/or of different people may be stored in the database, each one or more reference images linked to an identity of the specific person whose eye was imaged.

In a second, typically later stage (stage II), the identification stage, a person is instructed to look at direction Y and an identification image is obtained (step 306). Typically, the identification image is obtained by the same camera 103 (or a camera providing the same optical results) as the camera used to obtain the reference image.

In step (308) a processor (such as processor 102) determines if the one or more identification image (the image obtained in step 306) corresponds to the person, based on one or more reference image linked to the identity of the person (the image obtained in step 302). An identification of the person is issued based on the determination (step 310).

In some embodiments, in the determination step (step 308) the processor calculates the direction of gaze in the identification image by using reference images of individual I (e.g., by finding the rigid transformation of the identification image relative to individual I's reference image and using the same gaze tracking techniques described herein). Then the processor compares the calculated direction of gaze to the known gaze direction Y of the identification image. If the calculated direction of gaze matches the known direction of gaze Y, and the rigidly transformed identification image has a high correlation to the reference image, then the person is positively identified as individual I. In this context, high correlation (or 'highly correlated') means a result that is unlikely to appear when matching two unrelated retinal images. For example, a high Pearson correlation of the two images (or a sparse description of the images), or a high Pearson correlation of pixels sampled from the two images.

Figure 3B:
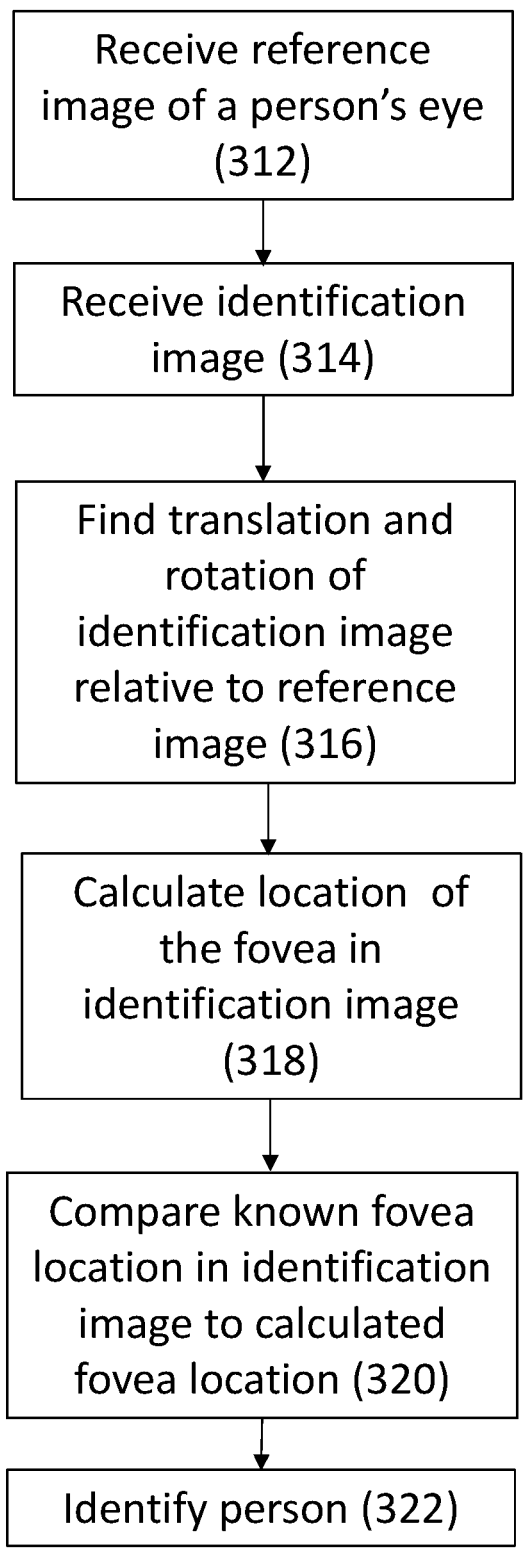
Figure 3B:
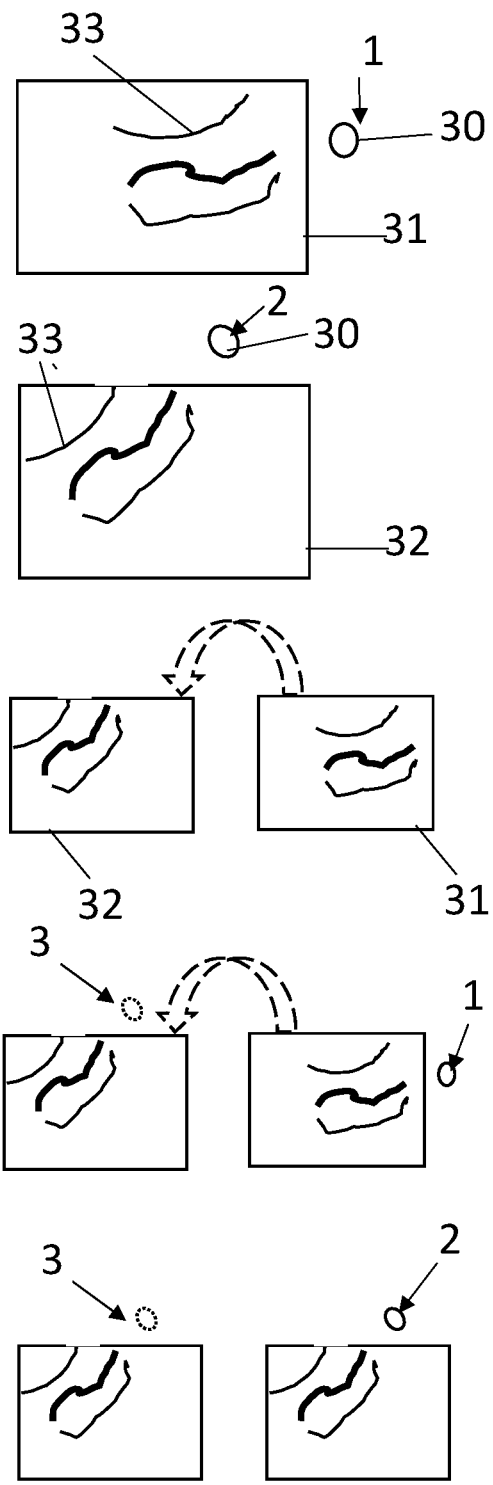

A method for biometric identification, according to an embodiment of the invention, is schematically illustrated in FIG. 3B.

In step 312 a processor (e.g., processor 102) receives a reference image 31 of at least a portion of a person's retina 33 while the person is looking at a first known direction. The location 1 of the fovea 30 of the reference image is known.

In step 314 an identification image 32 is received from an unidentified person. The identification image is obtained while the unidentified person is looking at a second direction of gaze. The location 2 of the fovea 30 of the identification image is known.

In step 316 a transformation (e.g., translation and/or rotation, represented by the dashed curved arrow) of the identification image 32 relative to the reference image 31 is found. If the identification image includes a different retina (or a different part of the retina) than the reference image, then no suitable transformation will be found, the process will abort and the person will not be identified.

In step 318 the processor calculates a predicted location 3 of the fovea in the identification image from the known fovea location 1 and by using the relative transformation (e.g., rotation and translation) calculated in step 316.

Known fovea location 2 and predicted fovea location 3 are compared, in step 320 and if known fovea location 2 and predicted fovea location 3 match, and the correlation strength of the transformed identification image relative to the reference image, is high (e.g., above a threshold) then the person is positively identified (step 322). If the locations don't match and/or the correlation strength is below a threshold, the person is not identified.

The threshold may be a predetermined threshold or, for example, a calculated threshold. For example, the threshold may include the likelihood of a random person being positively (but falsely) identified, as described above.

The above steps may be repeated using several reference images (e.g., as described herein). In some embodiments the steps above may be repeated for a sequence of identification images obtained while a person is gazing at a moving target.

The above steps may be performed using additional embodiments of the invention, e.g., by transforming reference and identification images and calculating a direction of gaze without calculating a location of the fovea, as described herein.

In some embodiments reference and identification images can be obtained and calculations as described above can be done for both eyes of the person.

For example, if one or more of the following conditions are fulfilled (for one or both eyes of the person) the identification issued in step 310 and/or step 322 could be considered a strongly positive biometric identification:

1. The pattern of the retina in an identification image of a person matches a pattern of the retina in a reference image linked to the identity of the same person.

2. The pattern of the retina and/or the predicted location of the fovea in an identification image obtained while the person is instructed to look at direction Y matches an expected transformation (e.g., translation and rotation) of retina pattern and/or predicted location of fovea, based on a reference image obtained while the same person was looking at direction X. Since the retina must respond to the instructions to look at different directions, in a certain way which is natural only to a real person, in order for a person to be positively identified, the portion of retina of a specific person must strongly correlate to a specific reference image. This step provides protection against a malicious user utilizing, for example, images or recordings of another person's retina.

3. A sequence of identification images obtained while the person is gazing at a moving target matches a sequence of expected images and/or reference images.

Reference and identification images may be analyzed according to embodiments of the invention. In one embodiment the analysis includes finding a spatial transformation between the identification image and reference image, calculating a change in orientation of the eye based on the spatial transformation and determining, based on the change in orientation of the eye, that the reference image and input image originate from a retina of a same person. The analysis may include determining whether the change in orientation is consistent with gaze targets associated with each of the reference image and input image.

In some embodiments the reference image may include stitching of a plurality of retina images (also termed a panorama) which covers a larger area of the person's retina than a single retina image. The panorama may be linked to a known direction of gaze (and/or to a known location of the person's fovea). The identification image may include a portion of the retina obtained from the person while the person is looking at a known direction different than direction X or while the person is looking at an unknown direction. The identification image can be compared to the panorama image of the person's retina to search for a match, as described herein, and an identification of the person may be issued based on the match.

If the change in orientation (determined using known eye tracking methods and/or by using methods described herein) is consistent (as described above) with gaze targets associated with each of the reference image and input image, and the identification image is highly correlated with the reference image, the person is positively identified.

In some embodiments reference images and identification images are processed (e.g., flattened) prior to the step of matching or correlating input images to reference images, as explained below.

In some embodiments, biometric identification as described above may be used together with other methods of identification, such as RFID cards, fingerprints and three-dimensional face recognition. Combined, the chance of a false identification can be significantly lowered. For example, first, a fingerprint scanner may quickly, but with a degree of uncertainty, identify a person to be a specific person (or one of a small number of candidates) out of a large set of people. Then, a device, as described above, compares the person's retina images with the identified candidates for a more certain positive identification.

Figure 4A:
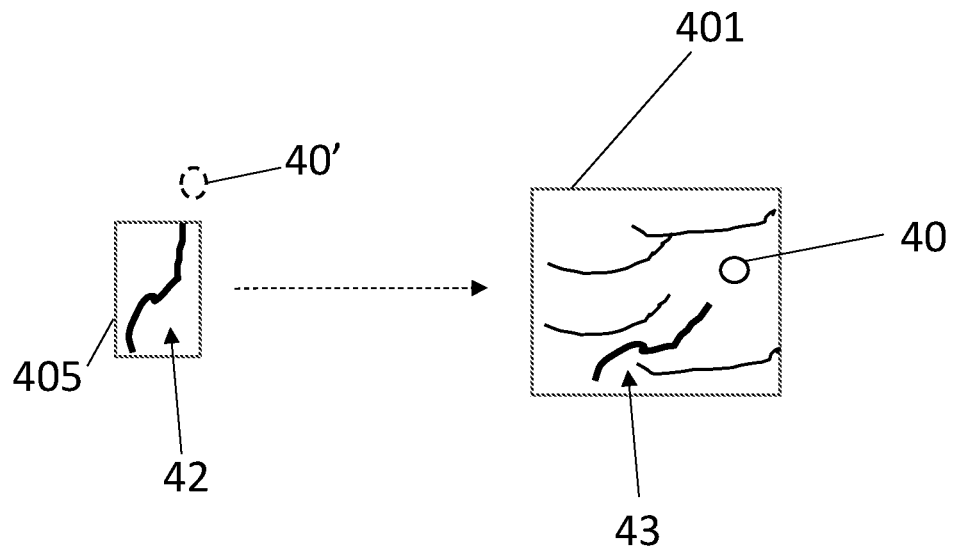
FIGS. 4A and 4B schematically illustrate maps linking images to fovea locations, according to embodiments of the invention.
Figure 4B:
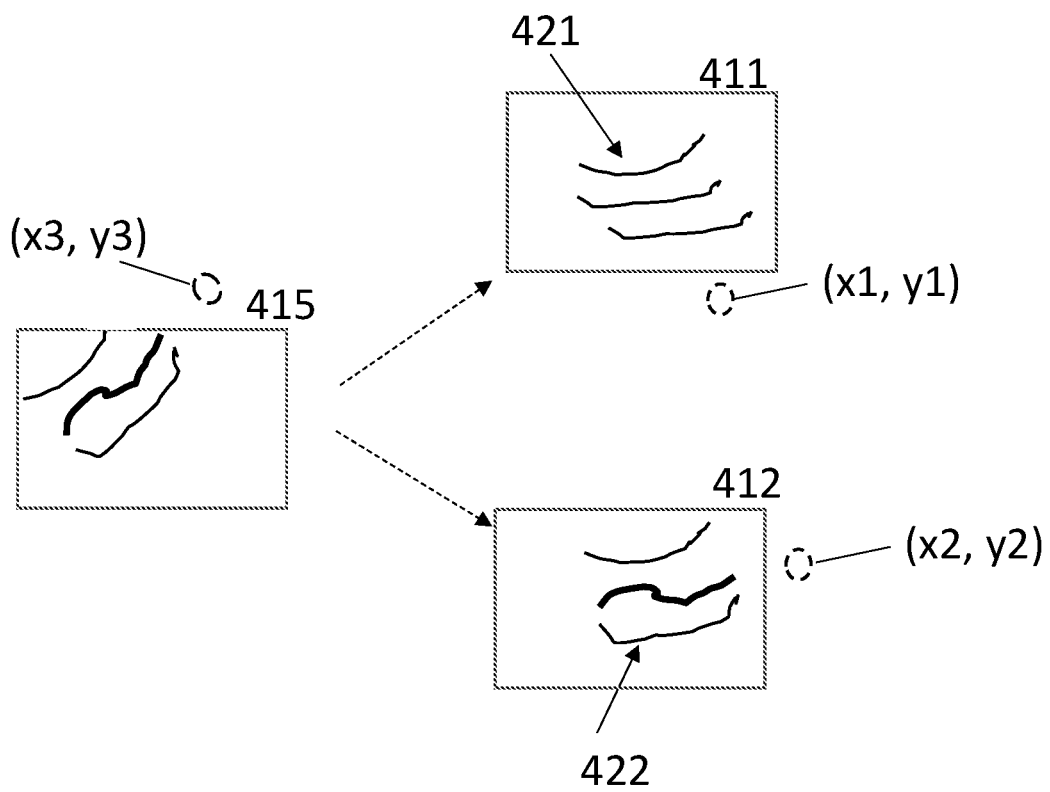

Referring now to FIGS. 4A and 4B, examples of maps and analyses, according to embodiments of the invention, which link portions of a person's retina, as imaged by a camera, to directions of gaze, will be schematically illustrated.

For example, one option of a map, which is schematically illustrated in FIG. 4A, includes creating a panorama image of the person's retina, which would serve as a reference image. The panorama image typically covers all or most parts of the retina that are visible to the camera in typically reasonable gaze directions. In one embodiment a panorama may be used to get a wider view of the retina, by asking the person to gaze at extreme angles.

The panorama image may or may not include the fovea. In this embodiment, several images of (possibly portions of) the retina are obtained without necessarily knowing the direction of gaze of the eye at the time each image was obtained. These images are then stitched together to build a panorama image 401 of the retina. The stitching may be done using standard techniques, such as feature matching and/or finding areas where two images share an area that is very similar (e.g. by Pearson correlation or square difference), merging the two into one image, and repeating until all images are merged to one. Before being stitched, the images may be projected to the surface of a 3D sphere as further described below. The fovea position relative to the panorama image 401 can be calculated from one or more images of portions of the retina (images that make up the panorama), for which the gaze direction is known.

An input image 405 is obtained while tracking the gaze of a person. The direction of gaze of the person is unknown at the time the input image 405 is obtained. Typically, input image 405 includes only a portion 45 of the retina 42 and does not include the fovea.

The input image 405 is compared to the panorama image 401 to find a match between the pattern of the retina 42 in input image 405, and the pattern of the retina 43 in the panorama image 401. The spatial transformation (e.g., translation and/or rotation) of the pattern of the retina 42 in image 405 relative to the pattern of the retina 43 in the panorama image 401, can be found. For example, processor 102 may identify features in the retina that appear both in the input image 405 and in the panorama image 401. The spatial correlation between the features in the panorama image 401 and in input image 405 may provide the required spatial transformation (e.g., translation and/or rotation) needed to align input image 405 with the panorama image 401. The location of fovea 40 can be transformed (e.g., translated and/or rotated) correspondingly, to obtain a calculated location of fovea 40'. The direction of gaze associated with input image 405 corresponds to the calculated location of fovea 40'.

In some embodiments, the camera imaging the person's eye is located at a distance from the eye that does not enable obtaining enough details for a reliable comparison of images (i.e. the image may falsely match other, unrelated, areas of the retina by chance). In this case, several input images are obtained in a small period of time (e.g., 1 second) at a high frame rate (e.g., 30 frames per second or higher), while the eye or camera is moving. The input images are stitched together. Typically, each consecutive input image will provide a slightly different view of the retina (either due to slight movement of the person's eye or due to slight movement of the camera) therefore stitching the several input images provides a single panoramic input image that covers a wider area of the retina. This panoramic input image can then be compared to the panorama image 401, as detailed above, to determine the person's direction of gaze associated with the period of time in which the several input images were obtained.

In other embodiments, a system imaging a person's eye from a distance of the eye may include a large diameter lens to capture a wider view. In another embodiment, the system images both eyes of a person (as described below), but from a distance, and determines possible directions of gaze of each eye, accepting only pairs of directions that coincide at a single gaze target. In other embodiments, a first, less accurate method, for determining gaze direction can be used, for example, using pupil location and/or pupil shape and/or corneal reflection. The more accurate method of determining direction of gaze using retinal images, according to embodiments of the invention, can be used on images resulting from the first method, thereby limiting the search space for spatial transformation between images, thereby allowing operation from a distance.

Another exemplary option of a map, which is schematically illustrated in FIG. 4B, includes a calibration step of obtaining images of portions of a person's retina at known directions of gaze. A map can be created by using a camera to obtain several images of the retina (or of a part of the retina) while the person looks at several, possibly arbitrary, but known, directions. A different image is obtained for each different direction. Each image is associated with a known direction of gaze. Taken together, these images comprise a map of reference images. For example, reference image 411 which includes a portion of the retina 421 corresponds to a first known direction of gaze and to a known or calculated location of the fovea (x1, y1). Reference image 412 includes a different portion of the retina 422 and corresponds to a second (and different) known direction of gaze and to a known or calculated location of the fovea (x2, y2).

An input image 415 (obtained in order to track the gaze of the person, while the direction of gaze is unknown), is then compared to the reference images 411 and 412 to identify a matching reference image, namely, a matching portion of the retina with a known direction of gaze. In the example illustrated in FIG. 4B, input image 415 matches reference image 412 (e.g., based on similar features). Once a matching reference image is found (reference image 412) the spatial transformation of the input image 415 relative to the matching reference image 412 can be found and applied to known or calculated location (x2, y2) of the fovea, to obtain calculated location (x3, y3) of the fovea relative to input image 415. A third (and different) direction of gaze can then be calculated for input image 415 from the calculated location (x3, y3) of the fovea.

Typically, input images and reference images are obtained using the same camera or a camera providing a similar optical result.

Maps or other constructs maintaining a link between a portion of the retina to a direction of gaze and/or to a known or calculated location of the person's fovea, may be stored in a storage device and may be accessed by processor 102 to determine directions of gaze according to embodiments of the invention.

Thus, some embodiments of the invention use the location of a person's fovea to determine a direction of gaze and to track the person's eye gaze.

As described above, the location of a person's fovea may be calculated based on the spatial transformation (e.g., translation and/or rotation of one or more feature) between an input and reference image.

In one embodiment a method includes calculating a location of the person's fovea in an input image based on the spatial transformation, to obtain a calculated location of fovea and based on the calculated location of fovea determining one or more of: orientation of the eye of the person, the direction of gaze, the gaze target and the ray of gaze, associated with the input image.

In one embodiment, a plurality of images of portions of retinas obtained at known directions of gaze (and optionally linked to known locations of the fovea) are used as training examples to a statistical model, such as a linear regression model, polynomial regression model, neural network, or suitable machine learning models.

In one embodiment calculating a change in orientation of the eye of the person can be done by using a statistical model trained on multiple pairs of a reference image and an input image. The statistical model can be trained on a plurality of spatial transformations between multiple pairs of a reference image and an input image. The model is trained with a goal of predicting a change in orientation of the eye of the person corresponding to each pair.

In one embodiment, a processor receives an input image including at least a portion of a person's retina and finds a spatial transformation between the input image and a reference image (the reference image also including at least a portion of the person's retina). The processor may provide the spatial transformation to a statistical model and, optionally, one or more of: a known orientation of the person's eye associated with the reference image, a known direction of gaze of the person associated with the reference image, a known gaze target associated with the reference image, and a known ray of gaze associated with the reference image. The statistical model trained on a collection of input parameters, each of the collection containing, e.g., at least a spatial transformation between a training reference image and a training input image, and each of the collection associated with an output parameter containing at least one of: a known orientation of an eye associated with the training input image, a known direction of gaze associated with the training input image, a known gaze target associated with the training input image, and a known ray of gaze associated with the training input image.

The statistical model can then be used to estimate at least one of: a change in orientation of the person's eye, an orientation of the person's eye associated with the input image, a direction of gaze associated with the input image, a gaze target associated with the input image and a ray of gaze associated with the input image.

In some embodiments processed images (e.g., flattened images, as described below) are used as training examples to the model. The model may then be used to predict a change in orientation of the eye of a person and/or a direction of gaze of the eye in an input image (e.g., an image of a portion of a retina of the eye at an unknown direction of gaze).

For example, a linear regression model may be used to predict gaze direction. The model is a matrix A, such that for a given set of input data x, the predicted gaze direction is Ax. Here, input data is all the information that is fed to the linear regression model and includes data from both the input image and the reference image and, e.g., the relative translation and rotation between them.

In order to train the model, a large set of images may be captured and the associated gaze target of the user may be recorded for each image. For each pair of all the captured retina images, one image serves as the input image and the other as the reference image. The two images are compared to find the spatial transformation in which the two images best align with each other, if any. A large set of spatial transformations can be obtained. For each spatial transformation i, a column of input data, $x_i$ and a column of target data, $y_i$ are produced. The input data may include, for example, the location of the pupil center in the input image; the location of the pupil center in the reference image; the gaze target when the reference image was obtained; parameters of the spatial transformation (e.g., relative translation and rotation) between input image and reference image. The target data may include the gaze target when the input image was obtained. Together, all the columns $x_i$ constitute a training input matrix X, and the columns $y_i$ constitute a training target matrix Y. Using linear regression, the matrix A that best maps X to Y is found. For an input image and reference image that produce input data x, the predicted gaze target is Ax. In another example, the input data, $x_i$ contains information about both eyes.

Models other than linear regression can be similarly used, for example polynomial regression, neural networks, machine learning models, or any other model that is trained from examples. All such models are referred to herein as statistical models.

For a single input image, the process may be repeated with different reference images. For each reference image, the model outputs a prediction. The average of the outputs (or any other statistic) may be used as a better estimate of the gaze direction, or the change of the orientation of the eye.

An input image typically includes a portion of a person's retina but does not include the person's fovea (since the person rarely looks directly at the camera) whereas reference images may or may not include the fovea, as described above.

Features that may be used to determine translation and rotation between an input image and a reference image may include lines, spots, edges, points and textures. These features may correspond to blood vessels and other biological structures visible in the retina.

Due to the way light is reflected and diffused within and from the surface of the eye, as discussed above, the signal corresponding to features on the retina, in images, may be very weak. Images of the retina may have uneven brightness levels. The images may include whiter and darker areas (which may be caused by uneven light from the light source, shadows from the iris, light reflection within the eye, refractions from the cornea or for other unknown reasons) that are not part of the pattern of the retina. These areas don't move together with the visible features of the retina (such as blood vessels) when the gaze direction is changed, and should therefore be ignored.

In some embodiments, in order to compare features between two retina images the images are processed, e.g., flattened, prior to the comparison. For example, the reference and input images may be flattened prior to finding the spatial transformation between them. In one example, the images may be processed to remove the areas of uneven brightness and flatten their intensity spatial distribution. One way to achieve this is by using a high pass filter on a raw input image or subtracting a blurred version of the raw input image from the original raw input image. Another way is by using a machine learning process (such as a CNN, for example a UNet CNN), trained to extract a flattened image of the retina from the raw input image. The machine learning process may be trained with a training set composed of typical raw retina images given as input to the learning process, and flattened retina images that serve as the target output that the learning process should produce. The flattened retina images in the training set may be drawn manually, identified manually on a high-pass image, or copied from a full retinal image obtained, for example, with a professional fundus camera.

Other processing methods can be used to obtain flattened images.

In one embodiment camera 103 obtains an input image of at least a portion of the person's retina and processor 102 obtains a processed input image, e.g., by flattening areas of uneven brightness in the input image. Processor 102 then compares the processed input image to a map linking known directions of gaze to previously obtained and processed reference images of the person's retina to determine the person's direction of gaze based on the comparison. A device (e.g., as detailed above) may be controlled based on the person's direction of gaze.

In some embodiments, comparing a processed image to a map linking known directions of gaze to previously processed images, to find the best correlating images may be done by calculating the highest Pearson correlation coefficient, as described above.

In some embodiments finding a spatial transformation between an input image and a reference image (possibly a processed (e.g., flattened) input image and processed reference image) includes trying multiple spatial transformations between the input image and reference image, calculating a similarity measure between the input image and reference image, corresponding to each spatial transformation, and choosing a spatial transformation based on the similarity measure. For example, the spatial transformation having the highest similarity measure can be chosen. A similarity measure could be a Pearson correlation coefficient, a mean of squared differences etc. and may be applied to the whole image, or to certain parts of it, as described above.

In one embodiment, input and reference images (and images of other objects emitting an angular pattern) can be more accurately aligned by mapping one to the other through a 3D spherical rotation (which is equivalent to a 3D rotation matrix). Each pixel in an image corresponds to an orientation, a direction in space. Each point on the retina also corresponds to an orientation because the eye works like a camera, where the retina is the sensor. Each orientation can be considered a unit vector and all possible unit vectors compose a surface of a unit sphere. An image from a camera can be thought of as lying on a patch of this sphere. Thus, in one embodiment of the invention, planar camera images are projected to a sphere and instead of (or in addition to) comparing the planar translation and rotation of two retina images, they are compared through a rotation of a sphere. Rotation of a sphere can be around any axis and is not limited just to 'roll'. A spherical rotation has three degrees of freedom that are analogous to the two degrees of freedom of planar translation plus the one degree of freedom of planar rotation.

Rotations of the eye around the gaze direction (torsional movements) do not change the gaze direction. Therefore, for gaze tracking purposes, finding the spherical rotation from a reference image to an input image is theoretically a two-degrees-of-freedom problem. However, the non-torsional component of the spherical rotation can be more accurately found if the rotation is not constrained to have no torsional component. Therefore, in some embodiments, a full three-degrees-of-freedom spherical rotation is used for aligning the reference image with the input image. Full three-degrees-of-freedom spherical rotations may also be used when stitching retinal images to form a panorama as described above.

Figure 5A:
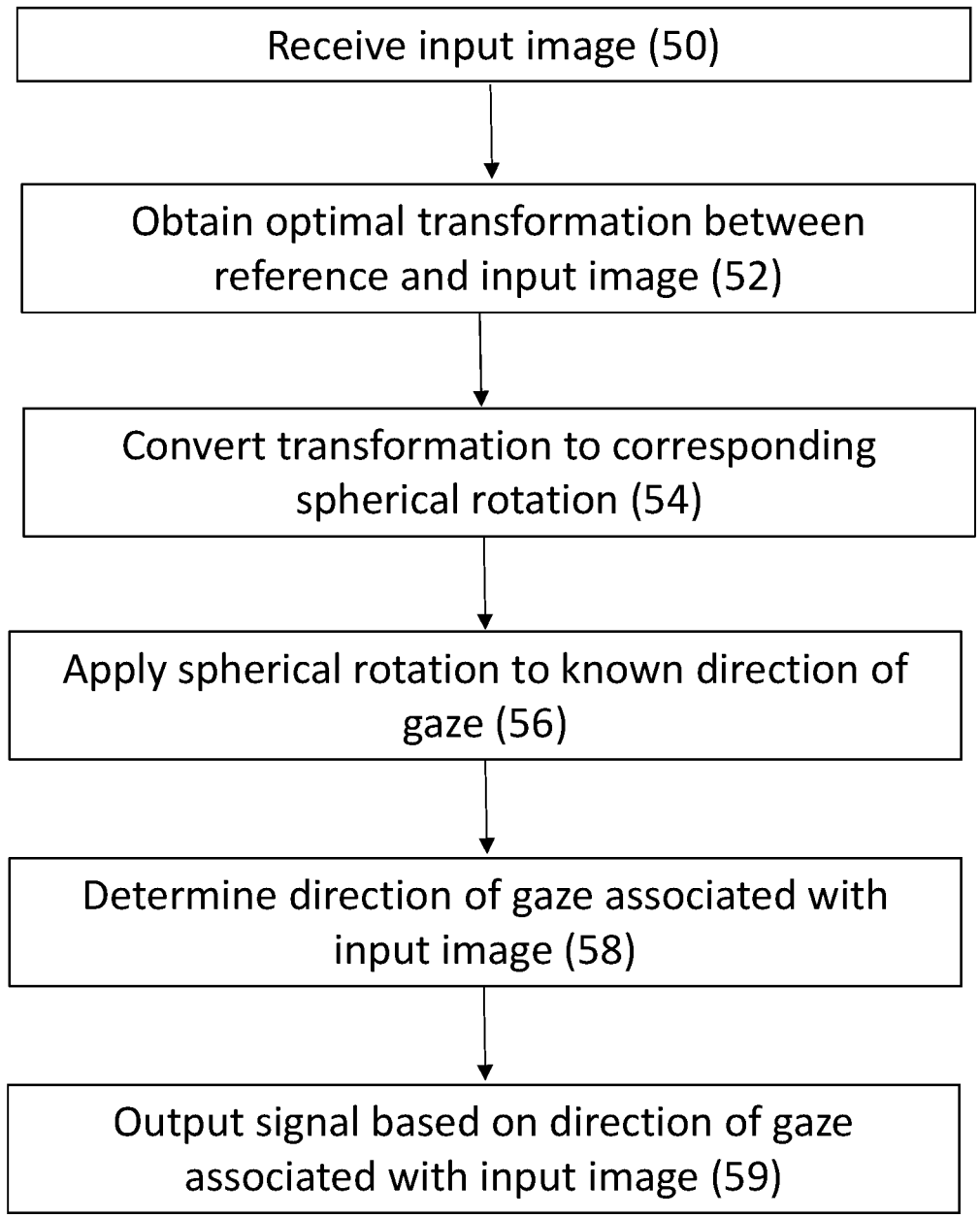
FIGS. 5A and 5B are schematic illustrations of methods for determining a direction of gaze of a person using rotations of a sphere, according to embodiments of the invention.

In an exemplary embodiment, which is schematically illustrated in FIG. 5A, a processor, such as processor 102 carries out a method for determining a direction of gaze of a person, which includes receiving an input image, which includes at least a portion of the person's retina at an unknown direction of gaze (step 50). The processor then finds a spatial transformation that optimally matches a reference image, which includes at least a portion of the person's retina at a known direction of gaze, with the input image (step 52). The spatial transformation is then converted to a corresponding spherical rotation (step 54), and the spherical rotation is applied to the known direction of gaze (step 56) to determine the direction of gaze associated with the input image (step 58). Optionally the spherical rotation can be applied to one or more of: orientation of the eye of the person, direction of gaze, gaze target and ray of gaze, associated with the input image.

A signal may be output (step 59) based on the person's direction of gaze associated with the input image. The signal may be used to control a device, such as described above.

This embodiment may be exemplified by the following equations:

$$R = f(T)$$

$$g_i = R g_r$$

Where T is a spatial transformation between images, R is the 3D spherical rotation between eye orientations, $f$ is a function, $g_r$ is the gaze direction associated with the reference image and $g_i$ is the gaze direction associated with the input image.

T can be, for example, a rigid planar transformation, or a 3D spherical rotation, in which case, $f(T) = T$. An example where T is a 3D spherical rotation follows.

In this example, a reference image $I_r$ is obtained. The reference image includes a person's eye looking at a known gaze target (known in the camera's frame of reference).

The position of the person's pupil center in the camera's frame of reference can be estimated from the image using known techniques. The pupil center is used as an estimate of the origin of the ray of gaze. The vector connecting the center of the pupil and the gaze target is normalized. The normalized vector is the reference gaze direction, $g_r$.

An input image $I_i$ of the person's eye is then obtained.

The coordinates of the camera sensor pixels are projected to a sphere. For example, in case of a pinhole camera, the projection is:

$$P: (x, y) \rightarrow \frac{(-x, -y, f)}{\sqrt{x^2 + y^2 + f^2}},$$

where $f$ is the focal length of the camera, and (0,0) is the pixel corresponding to the optical center of the camera. In a camera with lens distortion, the pixel position may be first corrected (e.g., undistorted), $(x, y) \rightarrow (x', y')$ before projecting to the sphere as in a pinhole camera, $$(x', y') \rightarrow \frac{(-x, -y', f)}{\sqrt{(x'^2 + y'^2 + f^2)}}.$$

For example, $(x', y')=((1+kr^2)x, (1+kr^2)y)$ where $r^2=x^2+y^2$ and k is the first radial distortion coefficient of the camera lens.

The inverse projection is $$P^{-1}: (x, y, z) \rightarrow \left( \frac{-xf}{z}, \frac{-yf}{z} \right).$$

For a 3×3 matrix, T, representing a candidate spherical rotation between the images, $I_r$ is compared with $I_i$ as follows: A retinal feature in $I_r$ with pixel coordinates (x, y) is compared with the retinal feature of $I_i$ with pixel coordinates $P^{-1}TP(x, y)$.

Of all candidates T, the 3D spherical rotation that maximizes the agreement between retinal features of $I_r$ at (x, y) with the retinal features of $I_i$ at $P^{-1}TP(x, y)$, for all relevant (x, y), is sought. Denote this maximizing rotation as $T_{max}$. All relevant pixels could mean, for example, all (x, y) in regions where there are retinal features in $I_r$.

$g_i = T_{max} g_r.$

This is the calculated gaze direction of the person associated with the input image and represented in the camera frame of reference.

The center of the pupil in $I_i$ is found. The gaze ray associated with $I_i$ is $g_i$ emanating from the pupil center.

Figure 5B:
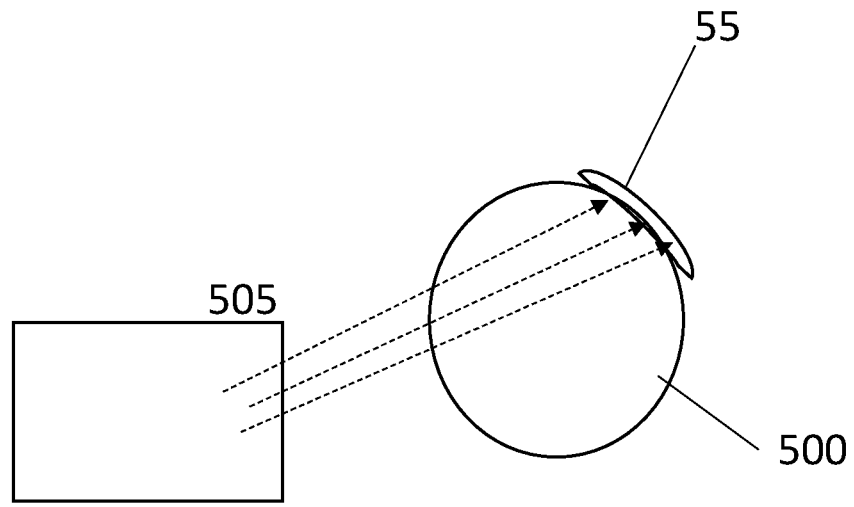
Figure 5B:
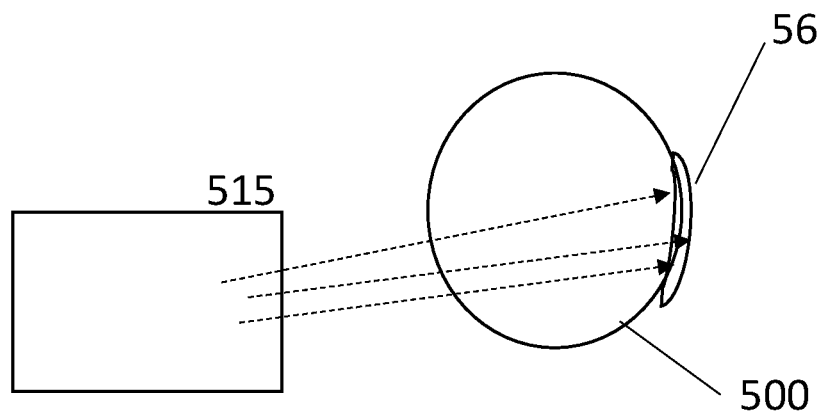

In an embodiment, which is schematically illustrated in FIG. 5B, the input image and the reference image are planar images and a processor may project a planar input image to a sphere to obtain a spherical input image and project a planar reference image to a sphere to obtain a spherical reference image, and find a spherical rotation between the spherical reference image and the spherical input image.

In another embodiment, the processor may find a planar rigid transformation between a planar input image and a planar reference image and convert the planar rigid transformation to a corresponding spherical rotation.

A reference image 505 is obtained by camera 103. The reference image 505 is planar and includes at least a portion of the eye's retina at a known direction of gaze. As described above, the reference image may be a panorama of large portions of the retina or a single image of a smaller portion of the retina. The reference image may or may not include the fovea. The reference image 505 is projected to a sphere 500 to create patch 55.

An input image 515 is obtained by camera 103 for tracking gaze of the eye. The input image 515 includes a portion of the retina at an unknown direction of gaze. The input image 515 is also projected to sphere 500 and creates patch 56.

Projecting images to a sphere can be done by representing each pixel in the image as a unit vector on a sphere based on the optics of camera 103, for example, as described above.

Processor 102 then determines the 3D rotation of sphere 500 necessary to bring the spherical projection of input image 515 (patch 56) to overlap the spherical projection of reference image 505 (patch 55). The determined 3D rotation of the sphere corresponds to the change in the orientation of the eye from when the reference image 505 was obtained to when the input image 515 is obtained. Thus, a rotation of the eye between its orientations when image 505 was obtained to when image 515 is obtained, can be determined based on the calculated rotation of the sphere.

The direction of gaze is determined by the fovea and center of the eye's lens, both of which are part of the eye and rotate with it, thus, the ray of gaze performs the same rotation as the eye. Since the direction of gaze is known for the reference image 505, the direction of gaze for the input image can be determined based on the rotation of the eye.

Searching a match between reference images and input images, using 3D rotations of a sphere, assists in achieving highly accurate overlap between the two images.

Additionally, a reference image and an input image may include the same area of the retina, however, that doesn't mean the eye is gazing at the same target in both cases. If the areas of the retina that appear in the reference image and the input image are the same but rotated relative to each other, the fovea in each case is at a different location (unless the image rotation is around the fovea), and the direction of gaze is therefore different. Additionally, if the images are the same but appear in different locations on the image sensor (i.e. the pupil's position relative to the camera is different), the fovea's theoretical location is also different and the direction of gaze is therefore different. Thus, determining how the spatial transformation of images affects the eye's orientation, possibly using 3D rotations, according to embodiments of the invention, is important for accurate and reliable gaze tracking using retinal images.

Comparing an input image to a reference image can be time consuming if all possible rigid transformations or all 3D spherical rotations are applied to the input image and compared vs each and every reference image. Embodiments of the invention provide a more time efficient process of comparing reference images and input images.

In a first step, a match between a planar input image and a plurality of planar reference images is searched, typically by searching translations and rotations, and possible matching reference images are identified. In a second step, a match is searched between the spherical projection of the input image to spherical projections of reference images identified in the first step. Several iterations of each of the steps may be performed.

In another embodiment, a sparse description of retina images is used for the comparison between images. Alternatively or in addition, features that are invariant to rotations and translations (e.g., distances between unique retinal features) may be used for comparing input images to reference images.

In order to find a match between an input image and a reference image, many rigid transformations of the input image may need to be compared to the reference image. Each comparison may require going over each pixel in the input image. A typical retina image contains thousands or millions of pixels. A sparse description of images containing only several dozen or hundreds of descriptors would therefore take less time to compare. Additionally, as described above, using a sparse description of images is useful in reducing false positives when searching for similar images.

Alternatively, or in addition, comparing only features that are invariant to rotations and translations, eliminates the need to repeat the comparison calculation for many rotations and translations. These embodiments may be used in addition to or instead of comparing entire high-resolution retinal images. These embodiments may be used for an initial fast search in a large bank of reference images. The best matches of the initial search may be chosen as candidates. The candidates may be later compared to the input image using a slower more accurate method to verify the match and calculate the spatial transformation (e.g., translation and rotation) between the input image and the reference images.

These embodiments provide a faster search of planar images and enable effectively searching a large image bank.

Similar methods may be used to provide a faster search of 3D spherical rotations when calculating a more accurate transformation between retina images (e.g., as described in FIGS. 5A and 5B).

Figure 6:
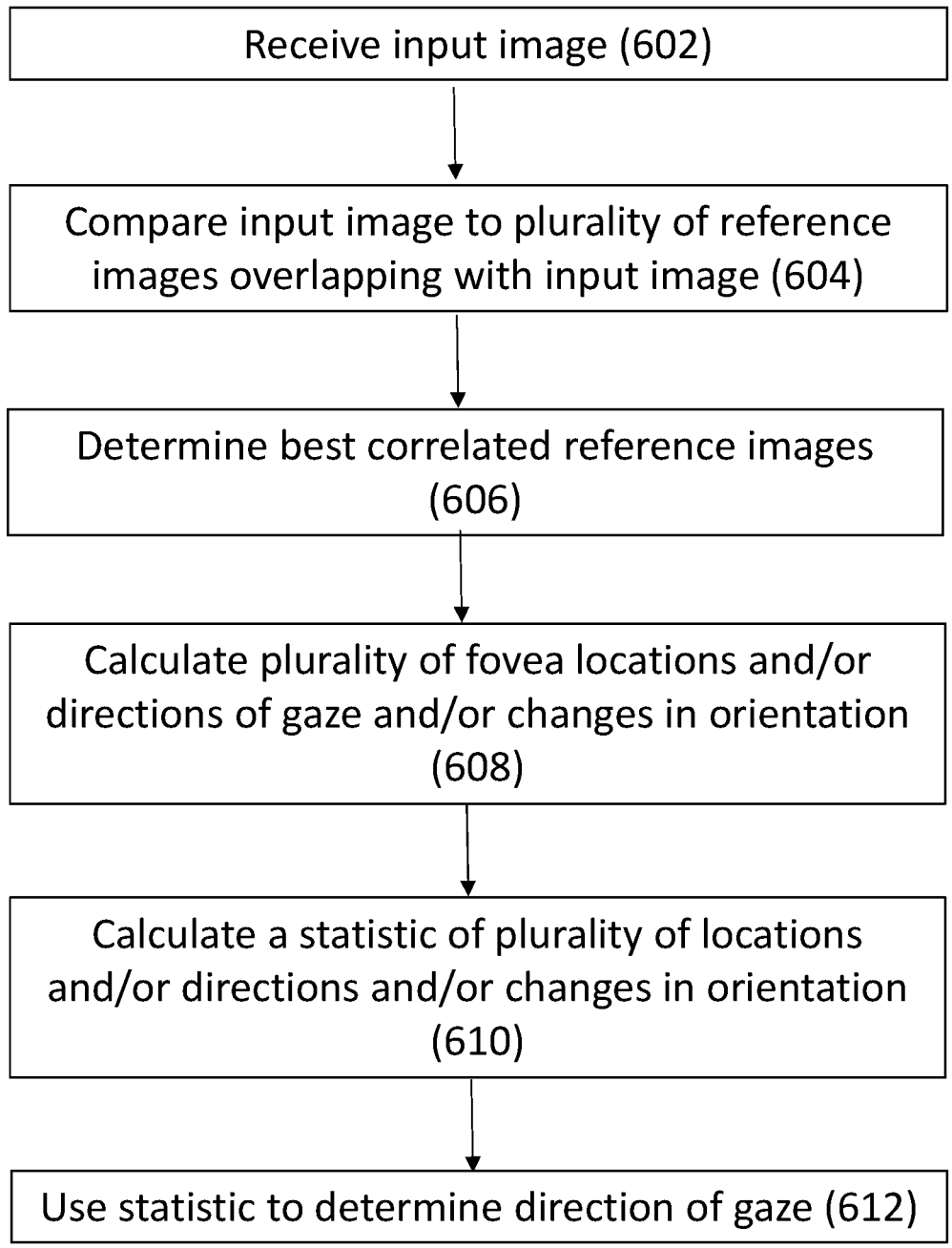
FIG. 6 schematically illustrates a method for comparing reference images and input images, according to an embodiment of the invention.

Embodiments of the invention provide high accuracy gaze direction determination, as schematically exemplified in FIG. 6.

Processor 102 receives an input image from camera 103 (step 602) and compares the input image to a plurality of previously obtained reference images to find reference images at least partially overlapping the input image (step 604). Processor 102 then determines a number of previously obtained reference images best correlated to the input image (step 606) and calculates the fovea locations and/or directions of gaze and/or change in orientation of the eye corresponding to the input image based on the best correlated reference images (608). The mean value, median value, average, or other appropriate statistic of the gaze directions and/or changes in orientation calculated from each reference image can be used as a more accurate approximation of the fovea location and/or direction of gaze and/or change in orientation. Thus, a statistic of the plurality of fovea locations and/or directions of gaze and/or changes in orientation is calculated (step 610) and the person's direction of gaze can be determined based on the statistic (step 612).

In another embodiment, processor 102 receives an input image from camera 103 and finds a plurality of spatial transformations between the input image and a plurality of reference images. Processor 102 calculates a statistic of the plurality of spatial transformations (e.g., mean value, median value, average, or other appropriate statistic) and determines one or more of: orientation of the eye of the person, the direction of gaze, the gaze target and the ray of gaze's direction of gaze, associated with the input image, based on the statistic.

In some embodiments, direction of gaze is determined based on input from both eyes of a person. In one embodiment, a system for determining gaze direction may include two cameras, one for each eye of the person. Alternatively, a single camera can obtain images of both eyes, e.g., by being positioned far enough so that both eyes are in its FoV or by using mirrors.

In some embodiments, two or more cameras are arranged to capture images of the same eye. In one embodiment, two or more cameras are used to capture images of one eye and none are used for the other eye. In another embodiment, two or more cameras are used for one eye, and one or more cameras are used to obtain images of the other eye.

In one embodiment at least one camera is configured to capture an image of a left eye of the person and at least one camera is configured to capture an image of a right eye of the person. A processor receiving images from the cameras calculates a change in orientation of the left eye and of the right eye. The processor can combine the change in orientation of the left eye and of the right eye to obtain a combined value and can then calculate one or more of: an orientation of the person's eyes, a direction of gaze of the person, a gaze target and a ray of gaze, based on the combined value.

In one embodiment the processor can associate with each of the left eye and the right eye, a ray of gaze, based on the change in orientation of the left eye and of the right eye. The processor may then determine an intersection point in space, of the ray of gaze associated with the left eye and the ray of gaze associated with the right eye. The distance of the intersection point from the person's eyes can be calculated, e.g., to determine distance/depth of a gaze target.

Figure 7:
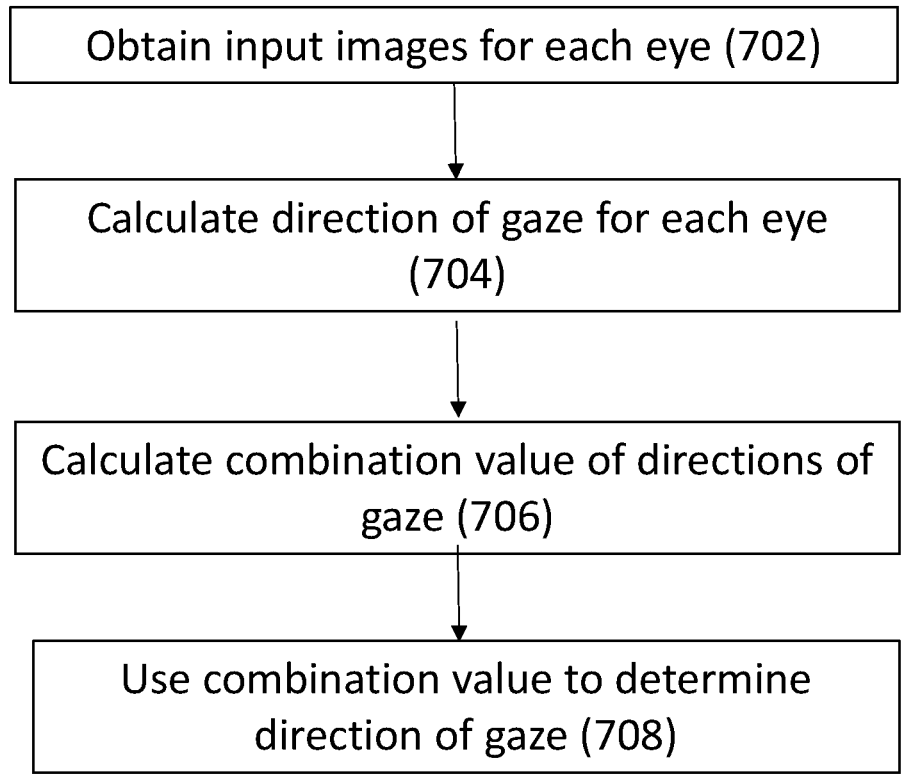
FIG. 7 schematically illustrates a method for determining a direction of gaze of a person based on input from both eyes of the person, according to embodiments of the invention.

In one embodiment, which is schematically illustrated in FIG. 7, a method for determining gaze direction includes obtaining simultaneous input images for each of a person's two eyes (702) and calculating a change in orientation for each eye separately (704), e.g., using methods described above. A combination value (e.g., an average) of the changes in orientations from both eyes is calculated (706) and the change in orientation of the person's eyes and/or direction of gaze is determined based on the combination value (708).

Thus, for example, a method for determining a direction of gaze of a person based on both eyes of a person, includes obtaining a reference image of each eye, which includes at least a portion of the eye's retina at a known direction of gaze and receiving an input image of each of the both eyes of the person, the input image including at least a portion of the eye's retina at an unknown direction of gaze. The method further includes finding a spatial transformation of the input image relative to the reference image and determining a direction of gaze of each of the both eyes based on the transformation. A combination value of the directions of gaze of both eyes of the person would then be calculated and the person's direction of gaze would be determined based on the combination value.

In some embodiments a statistical model (e.g., as described above) can be used to predict first and second eye directions of gaze based on the spatial transformation between a reference image which includes at least a portion of the first eye's retina relative to an input image which includes at least a portion of the first eye's retina and based on the spatial transformation between a reference image which includes at least a portion of the second eye's retina relative to an input image which includes at least a portion of the second eye's retina. A combination value of the first and second directions of gaze can be calculated and the person's direction of gaze can be determined based on the calculated combination value.

In another embodiment, a single statistical model is used to predict a direction of gaze of the person based on data from the input image and reference image of the first eye, and data from the input image and reference image of the second eye. For example, one model accepts as input two spatial transformations, one transformation associated with each eye, and outputs a single prediction of direction of gaze. The input data to the model, may include, for example, the location of the pupil center in the input image of each eye; the location of the pupil center in the reference image of each eye; the gaze target in the reference image of each eye; the rigid transformation for each eye between input image and reference image, etc.

In some embodiments, a statistical model may be used to predict a direction of gaze of each eye based on the spatial transformation of the input image relative to the reference image. A combination value of the direction of gaze of each eye may then be calculated and the person's direction of gaze can be determined based on the combination value.

In another embodiment, gaze direction is determined by using a physical model for the head, including both eyes, with certain constraints. These constraints may be that each eye's location is fixed relative to the head, that both eyes gaze at the same point, and that eyes maintain a fixed roll (i.e. they do not rotate around the direction of gaze). The input parameters, such as the position of the pupils, and the relative rigid transformation between input image and reference image, are used as inputs to a probabilistic model that calculates the most likely values for parameters of the physical model given the inputs and the constraints.

The invention claimed is:

1. A method comprising:
receiving an input image including at least a portion of a person's retina;
finding a spatial transformation between the input image and a reference image, the reference image including at least a portion of the person's retina, the reference image associated with a known direction of gaze of the person;
converting the spatial transformation to a corresponding spherical rotation having three degrees of freedom;
using the spherical rotation to rotate the known direction of gaze associated with the reference image to calculate a change in orientation of an eye of the person corresponding to the spatial transformation; and
outputting a signal based on the change of orientation.

2. The method of claim 1 wherein the reference image is associated with one or more of: a known orientation of the person's eye, a known gaze target and a known ray of gaze, the method further comprising the step of calculating, based on the reference image and the change in orientation, one or more of: an orientation of the person's eye associated with the input image, a direction of gaze associated with the input image, a gaze target associated with the input image and a ray of gaze associated with the input image.

3. The method of claim 2 comprising:
calculating a location of the person's fovea in the input image based on the spatial transformation, to obtain a calculated location of fovea; and
determining one or more of: orientation of the eye of the person, the direction of gaze, the gaze target and the ray of gaze, associated with the input image, based on the calculated location of fovea.

4. The method of claim 1 wherein the reference image comprises a plurality of images of portions of the person's retina stitched together to build a panorama image of the retina.

5. The method of claim 1 wherein the step of finding a spatial transformation between the input image and a reference image comprises:
trying multiple spatial transformations between the input image and reference image;
calculating a similarity measure between the input image and reference image corresponding to each spatial transformation; and
choosing a spatial transformation based on the similarity measure.

6. The method of claim 1 wherein the input image and the reference image are planar images, the method comprising:
projecting a planar input image to a sphere to obtain a spherical input image;
projecting a planar reference image to a sphere to obtain a spherical reference image; and
finding the spherical rotation between the spherical reference image and the spherical input image.

7. The method of claim 1 comprising:
finding a planar rigid transformation between a planar input image and a planar reference image; and
converting the planar rigid transformation to a corresponding spherical rotation.

8. The method of claim 1 comprising processing the input image and reference image to flatten the input image and reference image, prior to finding the spatial transformation.

9. The method of claim 2 comprising
finding a plurality of spatial transformations between the input image and a plurality of reference images;
calculating a statistic of the plurality of spatial transformations; and
determining one or more of: orientation of the eye of the person, the direction of gaze, the gaze target and the ray of gaze's direction of gaze, associated with the input image, based on the statistic.

10. The method of claim 1 wherein the reference image is associated with a first known gaze target and the input image is associated with a second known gaze target, the method further comprising:
if the change in orientation is consistent with gaze targets associated with each reference image and input image, then determining that the reference image and input image originate from a retina of a same person.

11. The method of claim 1 for use in matching an input image with a reference image to identify a user.

12. A system comprising:
at least one retinal camera comprising:
an image sensor to capture at least first and second images of a person's eye; and
a camera lens configured to focus light originating from the person's retina on the image sensor;
a light source producing light emanating from a location near the retinal camera; and
a processor to
find a spatial transformation between the first image and second image, the second image associated with a known direction of gaze of the person,
convert the spatial transformation to a corresponding spherical rotation having three degrees of freedom, and
use the spherical rotation to rotate the known direction of gaze associated with the second image to calculate a change in orientation of the person's eye between the first and second images captured by the image sensor.

13. The system of claim 12 wherein the processor is configured to calculate one or more of: an orientation of the person's eye, a direction of gaze of the person, a gaze target and a ray of gaze, based on the change in orientation of the person's eye between the first and second images.

14. The system of claim 12 further comprising a beam splitter configured to direct light from the light source to the person's eye.

15. The system of claim 12 wherein the light source is a polarized light source, the system further comprising a polarizer configured to block light originating from the light source and reflected through specular reflection.

16. The system of claim 12 wherein the light source comprises at least one infra-red LED.

17. The system of claim 12 wherein at least one retinal camera is configured to capture an image of a left eye of the person and at least one retinal camera is configured to capture an image of a right eye of the person and wherein the processor is configured to calculate a change in orientation of the left eye and of the right eye.

18. The system of claim 17 wherein the processor is configured to combine the change in orientation of the left eye and of the right eye to obtain a combined value and to calculate one or more of: an orientation of the person's eyes, a direction of gaze of the person, a gaze target and a ray of gaze, based on the combined value.

19. The system of claim 17 wherein the processor is configured to:
  associate with each of the left eye and the right eye, a ray of gaze, based on the change in orientation of the left eye and of the right eye;
  determine an intersection point in space of the ray of gaze associated with the left eye and the ray of gaze associated with the right eye; and
  calculate a distance of the intersection point from the person's eyes.

* * * * *